(12) United States Patent
Langes et al.

(10) Patent No.: US 10,954,235 B2
(45) Date of Patent: Mar. 23, 2021

(54) CRYSTALLINE FORMS OF VALBENAZINE SALTS

(71) Applicant: Sandoz AG, Basel (CH)

(72) Inventors: Christoph Langes, Innsbruck (AT); Ulrich Griesser, Innsbruck (AT); Erwin Schreiner, Kundl (AT); Marijan Stefinovic, Kundl (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 16/488,735

(22) PCT Filed: Feb. 1, 2018

(86) PCT No.: PCT/EP2018/052496
§ 371 (c)(1),
(2) Date: Aug. 26, 2019

(87) PCT Pub. No.: WO2018/153632
PCT Pub. Date: Aug. 30, 2018

(65) Prior Publication Data
US 2020/0062750 A1   Feb. 27, 2020

(30) Foreign Application Priority Data

Feb. 27, 2017 (EP) .................................. 17158207
Mar. 24, 2017 (EP) .................................. 17162804
Apr. 11, 2017 (EP) .................................. 17165954

(51) Int. Cl.
*C07D 471/06* (2006.01)
*A61K 31/4745* (2006.01)
*C07D 471/04* (2006.01)

(52) U.S. Cl.
CPC ........ *C07D 471/04* (2013.01); *C07B 2200/13* (2013.01)

(58) Field of Classification Search
CPC .................. A61K 31/4745; C07D 471/06
USPC ........................................... 546/94; 514/295
See application file for complete search history.

(56) References Cited

FOREIGN PATENT DOCUMENTS

| WO | 2008058261 A1 | 5/2008 |
| WO | 2010044981 A2 | 4/2010 |
| WO | 2011153157 A3 | 4/2012 |
| WO | 2014120654 A1 | 8/2014 |
| WO | 2015084622 A1 | 6/2015 |
| WO | 2015171802 A1 | 11/2015 |
| WO | 2016210180 A2 | 12/2016 |

OTHER PUBLICATIONS

International Search Report and Written Opinion for PCT/EP2018/052496, dated Aug. 30, 2018, 10 pages.
Brossi, A., et al., Helvetica Chimica Acta, 1958, 41(1), p. 119, abstract Wiley Online Library.
O'Brien, Christopher F., et al., NBI-98854, Movement Disorders, vol. 30, No. 12, 2015, pp. 1681-1687.
Pecharsky, et al., Fundamentals of Powder Diffraction and Structural Characterization of Materials, Springer, 2005, p. 3.

*Primary Examiner* — Charanjit Aulakh
(74) *Attorney, Agent, or Firm* — Luedeka Neely Group, P.C.

(57) ABSTRACT

The present invention relates to crystalline valbenazine ditosylate, in particular to a crystalline hydrate of valbenazine ditosylate and a crystalline anhydrate of valbenazine ditosylate, and to methods for their preparation. Furthermore, the invention relates to a pharmaceutical composition comprising the crystalline hydrate or the crystalline anhydrate, preferably in an effective and/or predetermined amount and to the use of said pharmaceutical composition as a medicament, in particular for the treatment of hyperkinetic movement disorders such as tardive dyskinesia.

Figure 1

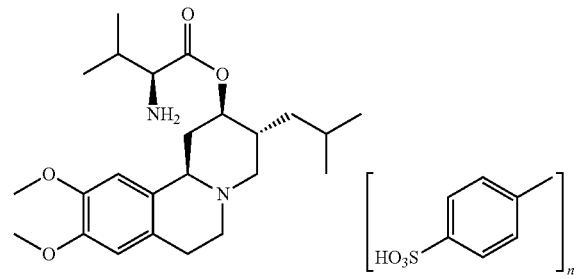

12 Claims, 9 Drawing Sheets

CRYSTALLINE FORMS OF VALBENAZINE SALTS

This application is a Section 371 national phase entry of PCT application PCT/EP2018/052496, filed Feb. 1, 2018. This application also claims the benefit of the earlier filing dates of European patent application 17158207.5, filed Feb. 27, 2017, European patent application 17162804.3, filed Mar. 24, 2017, and of European patent application 17165954.3, filed Apr. 11, 2017.

FIELD OF THE INVENTION

The present invention relates to pharmaceutically acceptable crystalline salts of valbenazine, such as valbenazine ditosylate, and in particular to a crystalline hydrate of valbenazine ditosylate and a crystalline anhydrate of valbenazine ditosylate, or such as crystalline valbenazine dihydrochloride, in particular to specific crystalline forms of valbenazine dihydrochloride, and to methods for their preparation. Furthermore, the invention relates to a pharmaceutical composition comprising the pharmaceutically acceptable crystalline salts of valbenazine, such as the crystalline hydrate of valbenazine ditosylate or the crystalline anhydrate of valbenazine ditosylate or specific crystalline forms of valbenazine dihydrochloride, preferably in an effective and/or predetermined amount and to the use of said pharmaceutical composition as a medicament, in particular for the treatment of hyperkinetic movement disorders such as tardive dyskinesia.

BACKGROUND OF THE INVENTION

Tardive dyskinesia (TD) is a persistent movement disorder induced by chronic neuroleptic exposure. Classical TD is characterized most commonly by involuntary movements of the orofacial region and choreoathetoid movements in the extremities and trunk, but other forms also exist [O'Brian C. F. et. al NBI-98854, A Selective Monoamine Transport Inhibitor for the Treatment of Tardive Dyskinesia: A Randomized, Double-Blind, Placebo-Controlled Study. Movement Disorders, Vol. 30, No. 12, 2015, 1681-1687]

Valbenazine, also known as NBI-98854, is a highly selective, vesicular monoamine transporter 2 (VMAT2) inhibitor in clinical development for the treatment of tardive dyskinesia. It is a L-valine (2R,3R,11bR)-1,3,4,6,7,11b-hexahydro-9,10-dimethoxy-3-(2-methylpropyl)-2H-benzo(a)quinolizin-2-yl ester and has the following chemical structure according to Formula I

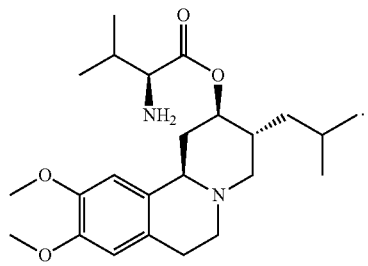

(I)

WO 2008/058261 A1 discloses the production of valbenazine as the free base (compound 2-1 in Example 2). The document further discloses the administration of single oral doses of valbenazine in 10% PEG in 0.25% methylcellulose in milli Q water to rats for pharmacokinetic evaluation (Example 6).

WO 2015/171802 A1 discloses oral administration of valbenazine to patients (Example 2). According to page 16, lines 16-17 of the document, valbenazine may be used in form of its dihydrochloride or ditosylate salt.

WO 2016/210180 A1 discloses oral administration of capsules containing valbenazine ditosylate to subjects in the course of a phase III clinical study (Example 4).

Most drug products are administered as oral dosage forms, and by far the most popular oral dosage forms are tablets because they are low in manufacturing costs, easy to handle, protect the drug substance against moisture and light, can be split into fractions if required, can be formulated as immediate or delayed release formulation, integrate quickly, are easy to swallow and usually well accepted by the patient.

Many compounds can exist in different solid forms. They can be in the amorphous or crystalline state and may exhibit (pseudo)polymorphism. When a compound is acidic or basic, it is often possible to create a salt, neutral compounds can build co-crystals. Such salts and co-crystals may also exist as various polymorphs, hydrates or solvates. These different solid forms possess different physical properties but not every solid form of a drug substance can be formulated into a tablet, since tableting requires suitable solid state properties of the drug substance such as physical and chemical stability, compatibility with excipients, sufficient bulk density, compressibility, flowability and wettability to mention just a few.

Hence, the objective of the present invention is to provide solid forms of valbenazine with suitable characteristics for a tablet formulation.

SUMMARY OF THE INVENTION

The present invention provides valbenazine ditosylate in crystalline form, in particular in form of a crystalline hydrate and in form of a crystalline anhydrate, which are especially suited to be used for a tablet formulation.

Aspects, advantageous features and preferred embodiments of the present invention are summarized in the following items:

1) Crystalline valbenazine ditosylate characterized by the chemical structure according to Formula VI

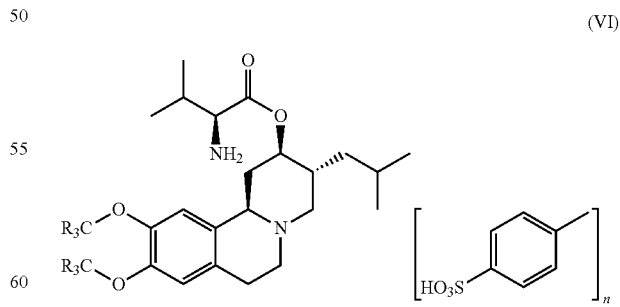

(VI)

wherein n is in the range of from 1.7 to 2.3; and R is H or D, preferably H.

2) The crystalline valbenazine ditosylate of item 1, which is an anhydrate or a hydrate, and wherein n is in the range of from 1.8 to 2.2.

3) The crystalline valbenazine ditosylate of item 1, which is an anhydrate or a hydrate, and wherein n is in the range of from 1.9 to 2.1.
4) The crystalline valbenazine ditosylate of item 1, which is an anhydrate or a hydrate, and wherein n is 1.7.
5) The crystalline valbenazine ditosylate of item 1, which is an anhydrate or a hydrate, and wherein n is 1.8.
6) The crystalline valbenazine ditosylate of item 1, which is an anhydrate or a hydrate, and wherein n is 1.9.
7) The crystalline valbenazine ditosylate of item 1, which is an anhydrate or a hydrate, and wherein n is 2.0.
8) The crystalline valbenazine ditosylate of item 1, which is an anhydrate or a hydrate, and wherein n is 2.1.
9) The crystalline valbenazine ditosylate of item 1, which is an anhydrate or a hydrate, and wherein n is 2.2.
10) The crystalline valbenazine ditosylate of item 1, which is an anhydrate or a hydrate, and wherein n is 2.3.
11) A crystalline hydrate of valbenazine ditosylate characterized by the chemical structure according to Formula VII

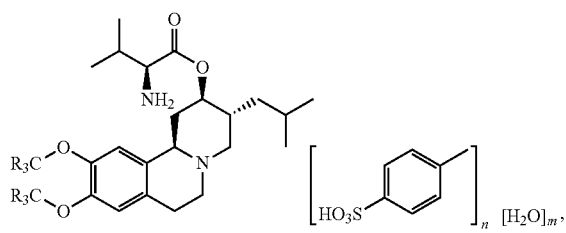

(VII)

wherein n is in the range of from 1.7 to 2.3; m is in the range of from 0.1 to 4.0; and R is H or D, preferably H.
12) A crystalline hydrate of valbenazine ditosylate of item 11, wherein n is in the range of from 1.8 to 2.2.
13) A crystalline hydrate of valbenazine ditosylate of item 11, wherein n is in the range of from 1.9 to 2.1.
14) A crystalline hydrate of valbenazine ditosylate of item 11, wherein n is 1.7.
15) A crystalline hydrate of valbenazine ditosylate of item 11, wherein n is 1.8.
16) A crystalline hydrate of valbenazine ditosylate of item 11, wherein n is 1.9.
17) A crystalline hydrate of valbenazine ditosylate of item 11, wherein n is 2.0.
18) A crystalline hydrate of valbenazine ditosylate of item 11, wherein n is 2.1.
19) A crystalline hydrate of valbenazine ditosylate of item 11, wherein n is 2.2.
20) A crystalline hydrate of valbenazine ditosylate of item 11, wherein n is 2.3.
21) A crystalline hydrate of valbenazine ditosylate according to any one of items 11 to 20, wherein m is in the range of from 0.2 to 3.8.
22) A crystalline hydrate of valbenazine ditosylate according to any one of items 11 to 20, wherein m is in the range of from 0.3 to 2.2.
23) A crystalline hydrate of valbenazine ditosylate according to any one of items 11 to 20, wherein m is in the range of from 0.5 to 1.6.
24) The crystalline valbenazine ditosylate as defined in any one of the preceding items characterized by having a powder X-ray diffractogram comprising reflections at 2-Theta angles of $(5.7\pm0.2)°$, $(16.0\pm0.2)°$ and $(18.6\pm0.2)°$, or of $(6.3\pm0.2)°$, $(17.9\pm0.2)°$ and $(19.8\pm0.2)°$, when measured at a temperature in the range of from 20 to 30° C. with Cu-Kalpha1,2 radiation having a wavelength of 0.15419 nm.
25) The crystalline valbenazine ditosylate as defined in any one of items 1 to 23 characterized by having a powder X-ray diffractogram comprising reflections at 2-Theta angles of $(5.7\pm0.2)°$, $(14.3\pm0.2)°$, $(16.0\pm0.2)°$ and $(18.6\pm0.2)°$, or of $(6.3\pm0.2)°$, $(15.6\pm0.2)°$, $(17.9\pm0.2)°$ and $(19.8\pm0.2)°$, when measured at a temperature in the range of from 20 to 30° C. with Cu-Kalpha1,2 radiation having a wavelength of 0.15419 nm.
26) The crystalline valbenazine ditosylate as defined in any one of items 1 to 23 characterized by having a powder X-ray diffractogram comprising reflections at 2-Theta angles of $(5.7\pm0.2)°$, $(10.2\pm0.2)°$, $(14.3\pm0.2)°$, $(16.0\pm0.2)°$ and $(18.6\pm0.2)°$, or of $(5.3\pm0.2)°$, $(6.3\pm0.2)°$, $(15.6\pm0.2)°$, $(17.9\pm0.2)°$ and $(19.8\pm0.2)°$, when measured at a temperature in the range of from 20 to 30° C. with Cu-Kalpha1,2 radiation having a wavelength of 0.15419 nm.
27) The crystalline valbenazine ditosylate as defined in any one of items 1 to 23 characterized by having a powder X-ray diffractogram comprising reflections at 2-Theta angles of $(5.7\pm0.2)°$, $(10.2\pm0.2)°$, $(14.3\pm0.2)°$, $(15.3\pm0.2)°$, $(16.0\pm0.2)°$ and $(18.6\pm0.2)°$, or of $(5.3\pm0.2)°$, $(6.3\pm0.2)°$, $(15.6\pm0.2)°$, $(16.6\pm0.2)°$, $(17.9\pm0.2)°$ and $(19.8\pm0.2)°$, when measured at a temperature in the range of from 20 to 30° C. with Cu-Kalpha1,2 radiation having a wavelength of 0.15419 nm.
28) The crystalline valbenazine ditosylate as defined in any one of items 1 to 23 characterized by having a powder X-ray diffractogram comprising reflections at 2-Theta angles of $(5.7\pm0.2)°$, $(10.2\pm0.2)°$, $(14.3\pm0.2)°$, $(15.3\pm0.2)°$, $(16.0\pm0.2)°$, $(16.9\pm0.2)°$ and $(18.6\pm0.2)°$, or of $(5.3\pm0.2)°$, $(6.3\pm0.2)°$, $(12.6\pm0.2)°$, $(15.6\pm0.2)°$, $(16.6\pm0.2)°$, $(17.9\pm0.2)°$ and $(19.8\pm0.2)°$, when measured at a temperature in the range of from 20 to 30° C. with Cu-Kalpha1,2 radiation having a wavelength of 0.15419 nm.
29) The crystalline valbenazine ditosylate as defined in any one of items 1 to 23 characterized by having a powder X-ray diffractogram comprising reflections at 2-Theta angles of $(5.7\pm0.2)°$, $(7.1\pm0.2)°$, $(10.2\pm0.2)°$, $(14.3\pm0.2)°$, $(15.3\pm0.2)°$, $(16.0\pm0.2)°$, $(16.9\pm0.2)°$ and $(18.6\pm0.2)°$, or of $(5.3\pm0.2)°$, $(6.3\pm0.2)°$, $(12.6\pm0.2)°$, $(12.8\pm0.2)°$, $(15.6\pm0.2)°$, $(16.6\pm0.2)°$, $(17.9\pm0.2)°$ and $(19.8\pm0.2)°$, when measured at a temperature in the range of from 20 to 30° C. with Cu-Kalpha1,2 radiation having a wavelength of 0.15419 nm.
30) The crystalline valbenazine ditosylate as defined in any one of items 1 to 23 characterized by having a powder X-ray diffractogram comprising reflections at 2-Theta angles of $(5.7\pm0.2)°$, $(7.1\pm0.2)°$, $(10.2\pm0.2)°$, $(14.3\pm0.2)°$, $(15.3\pm0.2)°$, $(16.0\pm0.2)°$, $(16.9\pm0.2)°$, $(17.9\pm0.2)°$ and $(18.6\pm0.2)°$, when measured at a temperature in the range of from 20 to 30° C. with Cu-Kalpha1,2 radiation having a wavelength of 0.15419 nm.
31) The crystalline valbenazine ditosylate as defined in any one of items 1 to 23 characterized by having a powder X-ray diffractogram comprising reflections at 2-Theta angles of $(5.7\pm0.2)°$, $(7.1\pm0.2)°$, $(10.2\pm0.2)°$, $(14.3\pm0.2)°$, $(15.3\pm0.2)°$, $(16.0\pm0.2)°$, $(16.9\pm0.2)°$, (17.9±0.2)°, (18.6±0.2)° and (22.6±0.2)°, when measured at a temperature in the range of from 20 to 30° C. with Cu-Kalpha1,2 radiation having a wavelength of 0.15419 nm.

32) The crystalline valbenazine ditosylate as defined in any one of items 1 to 23 characterized by having a powder X-ray diffractogram comprising reflections at 2-Theta angles of (5.7±0.1)°, (16.0±0.1)° and (18.6±0.1)°, or of (6.3±0.1)°, (17.9±0.1)° and (19.8±0.1)°, when measured at a temperature in the range of from 20 to 30° C. with Cu-Kalpha1,2 radiation having a wavelength of 0.15419 nm.

33) The crystalline valbenazine ditosylate as defined in any one of items 1 to 23 characterized by having a powder X-ray diffractogram comprising reflections at 2-Theta angles of (5.7±0.1)°, (14.3±0.1)°, (16.0±0.1)° and (18.6±0.1)°, or of (6.3±0.1)°, (15.6±0.1)°, (17.9±0.1)° and (19.8±0.1)°, when measured at a temperature in the range of from 20 to 30° C. with Cu-Kalpha1,2 radiation having a wavelength of 0.15419 nm.

34) The crystalline valbenazine ditosylate as defined in any one of items 1 to 23 characterized by having a powder X-ray diffractogram comprising reflections at 2-Theta angles of (5.7±0.1)°, (10.2±0.1)°, (14.3±0.1)°, (16.0±0.1)° and (18.6±0.1)°, or of (5.3±0.1)°, (6.3±0.1)°, (15.6±0.1)°, (17.9±0.1)° and (19.8±0.1)°, when measured at a temperature in the range of from 20 to 30° C. with Cu-Kalpha1,2 radiation having a wavelength of 0.15419 nm.

35) The crystalline valbenazine ditosylate as defined in any one of items 1 to 23 characterized by having a powder X-ray diffractogram comprising reflections at 2-Theta angles of (5.7±0.1)°, (10.2±0.1)°, (14.3±0.1)°, (15.3±0.1)°, (16.0±0.1)° and (18.6±0.1)°, or of (5.3±0.1)°, (6.3±0.1)°, (15.6±0.1)°, (16.6±0.1)°, (17.9±0.1)° and (19.8±0.1)°, when measured at a temperature in the range of from 20 to 30° C. with Cu-Kalpha1,2 radiation having a wavelength of 0.15419 nm.

36) The crystalline valbenazine ditosylate as defined in any one of items 1 to 23 characterized by having a powder X-ray diffractogram comprising reflections at 2-Theta angles (5.7±0.1)°, (10.2±0.1)°, (14.3±0.1)°, (15.3±0.1)°, (16.0±0.1)°, (16.9±0.1)° and (18.6±0.1)°, or of (5.3±0.1)°, (6.3±0.1)°, (12.6±0.1)°, (15.6±0.1)°, (16.6±0.1)°, (17.9±0.1)° and (19.8±0.1)°, when measured at a temperature in the range of from 20 to 30° C. with Cu-Kalpha1,2 radiation having a wavelength of 0.15419 nm.

37) The crystalline valbenazine ditosylate as defined in any one of items 1 to 23 characterized by having a powder X-ray diffractogram comprising reflections at 2-Theta angles of (5.7±0.1)°, (7.1±0.1)°, (10.2±0.1)°, (14.3±0.1)°, (15.3±0.1)°, (16.0±0.1)°, (16.9±0.1)° and (18.6±0.1)°, or of (5.3±0.1)°, (6.3±0.1)°, (12.6±0.1)°, (12.8±0.1)°, (15.6±0.1)°, (16.6±0.1)°, (17.9±0.1)° and (19.8±0.1)°, when measured at a temperature in the range of from 20 to 30° C. with Cu-Kalpha1,2 radiation having a wavelength of 0.15419 nm.

38) The crystalline valbenazine ditosylate as defined in any one of items 1 to 23 characterized by having a powder X-ray diffractogram comprising reflections at 2-Theta angles of (5.7±0.1)°, (7.1±0.1)°, (10.2±0.1)°, (14.3±0.1)°, (15.3±0.1)°, (16.0±0.1)°, (16.9±0.1)°, (17.9±0.1)° and (18.6±0.1)°, when measured at a temperature in the range of from 20 to 30° C. with Cu-Kalpha1,2 radiation having a wavelength of 0.15419 nm.

39) The crystalline valbenazine ditosylate as defined in any one of items 1 to 23 characterized by having a powder X-ray diffractogram comprising reflections at 2-Theta angles of (5.7±0.1)°, (7.1±0.1)°, (10.2±0.1)°, (14.3±0.1)°, (15.3±0.1)°, (16.0±0.1)°, (16.9±0.1)°, (17.9±0.1)°, (18.6±0.1)° and (22.6±0.1)°, when measured at a temperature in the range of from 20 to 30° C. with Cu-Kalpha1,2 radiation having a wavelength of 0.15419 nm.

40) The crystalline valbenazine ditosylate as defined in any one of items 1 to 23 characterized by having a powder X-ray diffractogram essentially the same as shown in FIG. 1 or FIG. 4 of the present invention, when measured at a temperature in the range of from 20 to 30° C. with Cu-Kalpha1,2 radiation having a wavelength of 0.15419 nm.

41) The crystalline valbenazine ditosylate as defined in any one of the preceding items characterized by having a DSC curve comprising an endothermic peak with an onset temperature of about 131° C. and a peak temperature of about 148° C., or by having a DSC curve comprising an endothermic peak with an onset temperature of about 239° C. and a peak temperature of about 242° C., when measured at a heating rate of 10 K/min.

42) The crystalline valbenazine ditosylate as defined in any one of items 1 to 40 characterized by having a DSC curve comprising an endothermic peak with an onset temperature of (131±2)° C. and a peak temperature of about (148±2)° C., or by having a DSC curve comprising an endothermic peak with an onset temperature of about (239±2)° C. and a peak temperature of about (242±2)° C., when measured at a heating rate of 10 K/min.

43) The crystalline valbenazine ditosylate as defined in any one of items 1 to 40 characterized by having a DSC curve comprising an endothermic peak with an onset temperature of (131±1)° C. and a peak temperature of about (148±1)° C., or by having a DSC curve comprising an endothermic peak with an onset temperature of about (239±1)° C. and a peak temperature of about (242±1)° C., when measured at a heating rate of 10 K/min.

44) The crystalline valbenazine ditosylate as defined in any one of the preceding items characterized by exhibiting a mass change of at most 5.0 w-%, based on the weight of the crystalline valbenazine ditosylate, when measured with GMS at a RH in the range of from 5 to 80% and a temperature of (25.0±0.1)° C., or by having a TGA curve showing a mass loss of not more than 1.0 w-%, based on the weight of the crystalline form, when measured in the temperature range of from 25 to 140° C. at a heating rate of 10 K/min.

45) The crystalline valbenazine ditosylate as defined in any one of items 1 to 43 characterized by exhibiting a mass change of at most 4.9 w-%, based on the weight of the crystalline valbenazine ditosylate, when measured with GMS at a RH in the range of from 5 to 80% and a temperature of (25.0±0.1)° C., or by having a TGA curve showing a mass loss of not more than 0.5 w-%, based on the weight of the crystalline form, when measured in the temperature range of from 25 to 140° C. at a heating rate of 10 K/min.

46) The crystalline valbenazine ditosylate as defined in any one of items 1 to 43 characterized by exhibiting a mass change of at most 3.0 w-%, based on the weight of the crystalline valbenazine ditosylate, when measured with GMS at a RH in the range of from 20 to 70% and a temperature of $(25.0\pm0.1)°$ C., or by having a TGA curve showing a mass loss of not more than 0.3 w-%, based on the weight of the crystalline form, when measured in the temperature range of from 25 to 140° C. at a heating rate of 10 K/min.
47) The crystalline valbenazine ditosylate as defined in any one of items 1 to 43 characterized by exhibiting a mass change of at most 2.8 w-%, based on the weight of the crystalline valbenazine ditosylate, when measured with GMS at a RH in the range of from 20 to 70% and a temperature of $(25.0\pm0.1)°$ C.
48) The crystalline valbenazine ditosylate as defined in any one of items 1 to 43 characterized by exhibiting a mass change of at most 2.0 w-%, based on the weight of the crystalline valbenazine ditosylate, when measured with GMS at a RH in the range of from 20 to 60% and a temperature of $(25.0\pm0.1)°$ C.
49) The crystalline valbenazine ditosylate as defined in any one of items 1 to 43 characterized by exhibiting a mass change of at most 1.9 w-%, based on the weight of the crystalline valbenazine ditosylate, when measured with GMS at a RH in the range of from 20 to 60% and a temperature of $(25.0\pm0.1)°$ C.
50) The crystalline valbenazine ditosylate as defined in any one of items 1 to 43 characterized by exhibiting a mass change of at most 1.5 w-%, based on the weight of the crystalline valbenazine ditosylate, when measured with GMS at a RH in the range of from 25 to 55% and a temperature of $(25.0\pm0.1)°$ C.
51) The crystalline valbenazine ditosylate as defined in any one of items 1 to 43 characterized by exhibiting a mass change of at most 1.3 w-%, based on the weight of the crystalline valbenazine ditosylate, when measured with GMS at a RH in the range of from 25 to 55% and a temperature of $(25.0\pm0.1)°$ C.
52) A composition comprising the crystalline valbenazine ditosylate as defined in any one of the preceding items, which composition is essentially free of any other physical form of valbenazine ditosylate.
53) A composition comprising the crystalline valbenazine ditosylate as defined in any one of items 1 to 51, characterized by comprising at most 20 weight % of any other physical form of valbenazine ditosylate, based on the total weight of the composition.
54) A composition comprising the crystalline valbenazine ditosylate as defined in any one of items 1 to 51, characterized by comprising at most 10 weight % of any other physical form of valbenazine ditosylate, based on the total weight of the composition.
55) A composition comprising the crystalline valbenazine ditosylate as defined in any one of items 1 to 51, characterized by comprising at most 5 weight % of any other physical form of valbenazine ditosylate, based on the total weight of the composition.
56) A composition comprising the crystalline valbenazine ditosylate as defined in any one of items 1 to 51, characterized by comprising at most 2 weight % of any other physical form of valbenazine ditosylate, based on the total weight of the composition.
57) A composition comprising the crystalline valbenazine ditosylate as defined in any one of items 1 to 51, characterized by comprising at most 1 weight % of any other physical form of valbenazine ditosylate, based on the total weight of the composition.
58) The composition according to any one of items 52 to 58, wherein the any other physical form is amorphous valbenazine ditosylate.
59) A composition comprising at least 90 w-% of the crystalline valbenazine ditosylate as defined in any one of items 1 to 51, based on the total weight of the composition.
60) The composition of item 59 comprising less than 5 w-% amorphous valbenazine ditosylate, based on the total weight of the composition.
61) The composition of item 59 comprising less than 2 w-% amorphous valbenazine ditosylate, based on the total weight of the composition.
62) A composition comprising at least 95 w-% of the crystalline valbenazine ditosylate as defined in any one of items 1 to 51, based on the total weight of the composition.
63) The composition of item 62 comprising less than 4 w-% amorphous valbenazine ditosylate, based on the total weight of the composition.
64) The composition of item 62 comprising less than 2 w-% amorphous valbenazine ditosylate, based on the total weight of the composition.
65) A process for the preparation of crystalline valbenazine ditosylate as defined in any one of items 1 to 51 or the composition as defined in any one of items 52 to 64 comprising:
    (i) reacting valbenazine with p-toluenesulfonic acid monohydrate in toluene; and
    (ii) removing toluene from the reaction mixture of step (i).
66) The process of item 65, wherein 1.0 mol equivalent valbenazine is reacted with 1.7 to 2.3 mol equivalent p-toluene sulfonic acid.
67) The process of item 65, wherein 1.0 mol equivalent valbenazine is reacted with 1.8 to 2.2 mol equivalent p-toluene sulfonic acid.
68) The process of item 65, wherein 1.0 mol equivalent valbenazine is reacted with 1.7 mol equivalent p-toluene sulfonic acid.
69) The process of item 65, wherein 1.0 mol equivalent valbenazine is reacted with 1.8 mol equivalent p-toluene sulfonic acid.
70) The process of item 65, wherein 1.0 mol equivalent valbenazine is reacted with 1.9 mol equivalent p-toluene sulfonic acid.
71) The process of item 65, wherein 1.0 mol equivalent valbenazine is reacted with 2.0 mol equivalent p-toluene sulfonic acid.
72) The process of item 65, wherein 1.0 mol equivalent valbenazine is reacted with 2.1 mol equivalent p-toluene sulfonic acid.
73) The process of item 65, wherein 1.0 mol equivalent valbenazine is reacted with 2.2 mol equivalent p-toluene sulfonic acid.
74) The process of item 65, wherein 1.0 mol equivalent valbenazine is reacted with 2.3 mol equivalent p-toluene sulfonic acid.
75) The process according to any one of items 65 to 74, wherein the valbenazine ditosylate concentration of the reaction mixture obtained in step (i) is in the range of from 20 to 50 g/L.

76) The process according to any one of items 65 to 74, wherein the valbenazine ditosylate concentration of the reaction mixture obtained in step (i) is in the range of from 30 to 40 g/L.
77) The process according to any one of items 65 to 76, optionally comprising slurrying the reaction mixture obtained in step (i).
78) The process according to item 77, wherein slurrying is performed at a temperature in the range of from 20 to 100° C.
79) The process according to item 77, wherein slurrying is performed at a temperature in the range of from 20 to 80° C.
80) The process according to item 77, wherein slurrying is performed at a temperature in the range of from 20 to 60° C.
81) The process according to item 77, wherein slurrying is performed at a temperature in the range of from 20 to 40° C.
82) The process according to item 77, wherein slurrying is performed at a temperature in the range of from 20 to 30° C.
83) The process according to any one of items 77 to 82, wherein slurrying is performed for a period in the range of from 6 to 48 hours.
84) The process according to any one of items 77 to 82, wherein slurrying is performed for a period in the range of from 12 to 36 hours.
85) The process according to any one of items 65 to 84, wherein in step (ii) the toluene is removed at atmospheric pressure.
86) The process according to any one of items 65 to 84, wherein in step (ii) the toluene is removed at a pressure of at most 500 mbar.
87) The process according to any one of items 65 to 84, wherein in step (ii) the toluene is removed at a pressure of at most 100 mbar.
88) The process according to any one of items 65 to 84, wherein in step (ii) the toluene is removed at a pressure of at most 50 mbar.
89) The process according to any one of items 65 to 88, wherein in step (ii) the toluene is removed at a temperature in the range of from about 20 to 100° C.
90) The process according to any one of items 65 to 88, wherein in step (ii) the toluene is removed at a temperature in the range of from about 20 to 80° C.
91) The process according to any one of items 65 to 88, wherein in step (ii) the toluene is removed at a temperature in the range of from about 20 to 60° C.
92) The process according to any one of items 65 to 88, wherein in step (ii) the toluene is removed at a temperature in the range of from about 20 to 40° C.
93) The process according to any one of items 65 to 84, wherein in step (ii) the toluene is removed at a pressure of 30 mbar and a temperature of 40° C.
94) The process according to any one of items 65 to 93, further comprising drying the crystals obtained in step (ii).
95) The process according to item 94, wherein drying is performed at a temperature of 80° C. or less.
96) The process according to item 94, wherein drying is performed at a temperature of 60° C. or less.
97) The process according to item 94, wherein drying is performed at a temperature of 40° C. or less.
98) The process according to any one of items 94, wherein drying is performed at a temperature in the range of from 20 to 30° C.
99) The process according to any one of items 94 to 98, wherein drying is performed for a period in the range of from 1 to 72 hours.
100) The process according to any one of items 94 to 98, wherein drying is performed for a period in the range of from 2 to 48 hours.
101) The process according to any one of items 94 to 98, wherein drying is performed for a period in the range of from 4 to 24 hours.
102) The process according to any one of items 94 to 98, wherein drying is performed for a period in the range of from 6 to 18 hours.
103) Use of the crystalline valbenazine ditosylate as defined in any one of items 1 to 51 for the preparation of a pharmaceutical composition.
104) Use of the crystalline valbenazine ditosylate as obtained by the process according to any one of items 65 to 102 for the preparation of a pharmaceutical composition.
105) Use of the composition as defined in any one of items 52 to 59 for the preparation of a pharmaceutical composition.
106) Use of the composition as obtained by the process according to any one of items 65 to 102 for the preparation of a pharmaceutical composition.
107) The use according to any one of items 103 to 106, wherein the pharmaceutical composition is prepared by a wet or dry processing method.
108) The use according to item 107, wherein the wet processing method comprises wet granulation.
109) The use according to item 107, wherein the dry processing method comprises dry granulation or direct compression.
110) A pharmaceutical composition comprising the crystalline valbenazine ditosylate as defined in any one of items 1 to 51 and at least one pharmaceutically acceptable excipient.
111) A pharmaceutical composition comprising the composition as defined in any one of items 52 to 59 and at least one pharmaceutically acceptable excipient.
112) The pharmaceutical composition of item 110 or 111, comprising a predetermined and/or pharmaceutically effective amount of the crystalline valbenazine ditosylate as defined in any one of items 1 to 51.
113) The pharmaceutical composition according to item 112, wherein the predetermined and/or pharmaceutically effective amount of crystalline valbenazine is selected from the group consisting of 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg and 150 mg, calculated as water free valbenazine.
114) The pharmaceutical composition according to item 112, wherein the predetermined and/or pharmaceutically effective amount of crystalline valbenazine ditosylate is selected from the group consisting of 25 mg, 40 mg, 50 mg, 75 mg, 80 mg and 100 mg, calculated as water free valbenazine.
115) The pharmaceutical composition according to item 112, wherein the predetermined and/or pharmaceutically effective amount of crystalline valbenazine ditosylate is 40 mg or 80 mg, calculated as water free valbenazine.
116) The pharmaceutical composition as defined in any one of items 110 to 115, wherein the at least one pharmaceutically acceptable excipient is selected from the group consisting of binders, fillers, diluents, disintegrants, lubricants, glidants, coloring agents, flavouring agents, sweetening agents, emulsifying agents, dispersing agents, wetting agents, film coatings and combinations thereof 117) The pharmaceutical composition according to any one of items 111 to 116 which is an oral solid dosage form.

118) The pharmaceutical composition according to item 117, wherein the oral solid dosage form is a tablet.

119) The pharmaceutical composition according to item 118, wherein the tablet is a film-coated tablet.

120) The pharmaceutical composition according to item 117, wherein the oral solid dosage form is a capsule.

121) The pharmaceutical composition according to any one of items 111 to 120, which is administered once daily.

122) The pharmaceutical composition according to any one of items 111 to 121 for use as a medicament.

123) The pharmaceutical composition according to any one of items 111 to 121 for use in the treatment of a hyperkinetic disorder.

124) The use according to item 123, wherein the hyperkinetic disorder is tardive dyskinesia.

125) A pharmaceutical package comprising the pharmaceutical composition according to any one of items 110 to 121.

126) The pharmaceutical package according to item 125, further comprising a patient information booklet.

127) The pharmaceutical package according to item 126, wherein the patient information booklet comprises dosing information, side effect information and information describing the disease being treated.

128) The pharmaceutical package according to any one of items 125 to 127, wherein the packaging material reduces or prevents water exchange between the pharmaceutical composition and the environment.

In another aspect, the present invention relates to valbenazine dihydrochloride in crystalline form. In particular, the present invention relates to crystalline forms of valbenazine dihydrochloride, which are especially suited to be used for a tablet formulation.

For example, the present invention relates to a first crystalline form of valbenazine dihydrochloride, which is characterized by having a powder X-ray diffractogram comprising reflections at 2-Theta angles of (6.9±0.2)°, (7.2±0.2)°, (9.2±0.2)°, (12.7±0.2)° and (18.1±0.2)°, when measured at a temperature in the range of from 20 to 30° C. with Cu-Kalpha1,2 radiation having a wavelength of 0.15419 nm.

In addition, the invention relates to a second crystalline form of valbenazine dihydrochloride, which is characterized by having a powder X-ray diffractogram comprising reflections at 2-Theta angles of (12.0±0.2)°, (16.3±0.2)°, (18.8±0.2)°, (20.5±0.2)° and (21.5±0.2)°, when measured at a temperature in the range of from 20 to 30° C. with Cu-Kalpha1,2 radiation having a wavelength of 0.15419 nm.

Finally, the invention relates to a third crystalline form of valbenazine dihydrochloride, which is characterized by having a powder X-ray diffractogram comprising reflections at 2-Theta angles of (4.2±0.2)°, (4.7±0.2)°, (8.6±0.2)°, (9.5±0.2)° and (13.3±0.2)°, when measured at a temperature in the range of from 20 to 30° C. with Cu-Kalpha1,2 radiation having a wavelength of 0.15419 nm.

Abbreviations and Definitions

PXRD powder X-ray diffractogram
DSC differential scanning calorimetry
TGA thermogravimetric analysis
GMS gravimetric moisture sorption
RT room temperature
RH relative humidity
w-% weight percent
dm delta m=mass change The term "valbenazine" refers to the compound with the chemical name (S)-2-Amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester, which is represented by the chemical structure as depicted in Formula I of the present invention. In the present invention "valbenazine" indicates the free base form, where the nitrogen atoms are not protonated.

The term "valbenazine ditosylate" refers to the compound with the chemical name ((S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate) ditosylate, which is represented by the chemical structure as depicted in Formula II of the present invention, wherein n is in the range of from 1.7 to 2.3, preferably from 1.8 to 2.2, more preferably from 1.9 to 2.1 and most preferably n is 2.0. For example, n can be selected from the group consisting of 1.7, 1.8, 1.9, 2.0, 2.1, 2.2 and 2.3.

The term "valbenazine dihydrochloride" refers to the compound with the chemical name ((S)-(2R,3R,11bR)-3-isobutyl-9,10-dimethoxy-2,3,4,6,7,11b-hexahydro-1H-pyrido[2,1-a]isoquinolin-2-yl 2-amino-3-methylbutanoate) dihydrochloride, which is represented by the chemical structure as depicted in Formula (VIII) of the present invention, wherein n is in the range of from 1.7 to 2.3, preferably from 1.8 to 2.2, more preferably from 1.9 to 2.1 and most preferably n is 2.0. For example, n can be selected from the group consisting of 1.7, 1.8, 1.9, 2.0, 2.1, 2.2 and 2.3.

Deuterium (2H or D) is a stable and non-radioactive isotope of hydrogen which has approximately twice the mass of protium (1H or H), the most common isotope of hydrogen. Deuterium oxide (D2O or "heavy water") looks and tastes like H2O, but has different physical properties. Studies have also shown that the use of D2O can delay the growth of cancer cells and enhance the cytotoxicity of certain antineoplastic agents. Deuteration of pharmaceuticals to improve pharmacokinetics (PK), pharmacodynamics (PD) and toxicity profiles has been demonstrated previously with some classes of drugs. As used herein, the term "valbenazine ditosylate" also refers to the compound which is represented by the chemical structure as depicted in Formula IV or VI of the present invention, i.e. at least one of the protiums of the dimethoxy groups of the compound can be substituted by deuterium.

The term "is/are deuterium" when used to describe a given position in a molecule such as R or the symbol "D", when used to represent a given position in a drawing of a molecular structure, means that the specified position is enriched with deuterium above the naturally occurring distribution of deuterium. In one embodiment deuterium enrichment is no less than about 1%, in another no less than about 5%, in another no less than about 10%, in another no less than about 20%, in another no less than about 50%, in another no less than about 70%, in another no less than about 80%, in another no less than about 90%, or in another no less than about 98% of deuterium at the specified position.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods known to one of ordinary skill in the art, including mass spectrometry and nuclear magnetic resonance spectroscopy.

The term "hydrate" as used herein, refers to a crystalline solid were water is cooperated in or accommodated by the crystal structure, e.g. is part of the crystal structure or entrapped into the crystal (water inclusions). Thereby, water can be present in a stoichiometric or non-stoichiometric amount.

The term "hydrate of valbenazine ditosylate" refers to a compound which is represented by the chemical structure as depicted in Formula III, V or VII of the present invention, wherein R can be independently selected from H or D, and n and m are defined as below.

A "stoichiometric hydrate" according to the present invention is characterized by possessing a constant mole ratio of the host molecule (e.g. valbenazine ditosylate) and water over a range of different water activities. For example, a monohydrate displays a constant mole ratio of the host molecule and water of 1.0:0.9 to 1.1, preferably of 1.0:1.0, over a range of different water activities.

A "non-stoichiometric" hydrate according to the present invention is characterized in that the mole ratio of the host molecule (e.g. valbenazine ditosylate) and water varies continuously as a function of water activity. For example, the non-stoichiometric hydrate of valbenazine ditosylate of the present invention displays a variation in the water content of more than 2.0 mole equivalents, when measured with GMS in the range of from 0 to 80% RH.

The terms "anhydrous form" or "anhydrate" as used herein refer to a crystalline solid where no water is cooperated in or accommodated by the crystal structure. Anhydrous forms may still contain residual water, which is not part of the crystal structure but may be adsorbed on the surface or absorbed in disordered regions of the crystal. Typically, an anhydrous form does not contain more than 1.0 w-%, preferably not more than 0.5 w-% of water, based on the weight of the crystalline form. The water content can be determined by Karl-Fischer Coulometry and/or by thermogravimetric analysis (TGA), e.g. by determining the weight loss in the range of from 25 to 140° C. at a heating rate of 10 K/min.

The term "anhydrate of valbenazine ditosylate" refers to a compound which is represented by the chemical structure as depicted in Formula II, IV or VI of the present invention, wherein R can be independently selected from H or D, and n is defined as below.

The chemical structure as depicted in Formula V or VII of the present invention, wherein R is H, corresponds to the chemical structure as depicted in Formula III. Likewise, the chemical structure as depicted in Formula IV or VI of the present invention, wherein R is H, corresponds to the chemical structure as depicted in Formula II.

The term "deuterated valbenazine" refers to the compound with the chemical name (S)-2-Amino-3-methyl-butyric acid (2R,3R,11bR)-3-isobutyl-9,10-dimethoxy-1,3,4,6,7,11b-hexahydro-2H-pyrido[2,1-a]isoquinolin-2-yl ester, which is represented by the chemical structure as depicted in Formula I of the present invention, wherein the 9,10-dimethoxy groups are enriched with deuterium, i.e. at least one of the protiums of the dimethoxy groups is substituted by deuterium. Preferably, the deuterium enrichment is no less than about 98% of deuterium at this position.

As used herein, the term "room temperature" refers to a temperature in the range of from 20 to 30° C. As used herein, the term "measured at a temperature in the range of from 20 to 30° C." refers to a measurement under standard conditions. Typically, standard conditions mean a temperature in the range of from 20 to 30° C., i.e. at room temperature. Standard conditions can mean a temperature of about 22° C. Standard conditions can also mean a temperature of about 25° C. Typically, standard conditions can additionally mean a measurement under 20-80% relative humidity, preferably 30-70% relative humidity, more preferably 40-60% relative humidity and most preferably 50% relative humidity.

The term "reflection" with regard to powder X-ray diffraction as used herein, means peaks in an X-ray diffractogram, which are caused at certain diffraction angles (Bragg angles) by constructive interference from X-rays scattered by parallel planes of atoms in solid material, which are distributed in an ordered and repetitive pattern in a long-range positional order. Such a solid material is classified as crystalline material, whereas amorphous material is defined as solid material, which lacks long-range order and only displays short-range order, thus resulting in broad scattering. According to literature, long-range order e.g. extends over approximately 103 to 1020 atoms, whereas short-range order is over a few atoms only (see "Fundamentals of Powder Diffraction and Structural Characterization of Materials" by Vitalij K. Pecharsky and Peter Y. Zavalij, Kluwer Academic Publishers, 2003, page 3).

The term "amorphous" as used herein refers to a solid form of a compound that is not crystalline. An amorphous compound possesses no long-range order and does not display a definitive X-ray diffraction pattern with reflections.

The term "essentially the same" with reference to PXRD means that variabilities in peak positions and relative intensities of the peaks are to be taken into account. For example, a typical precision of the 2-Theta values is in the range of ±0.2° 2-Theta, preferably in the range of ±0.1° 2-Theta. Thus, a diffraction peak that usually appears at 5.7° 2-Theta for example can appear between 5.5° and 5.9° 2-Theta, preferably between 5.6° and 5.8° 2-Theta on most X-ray diffractometers under standard conditions. Furthermore, one skilled in the art will appreciate that relative peak intensities will show inter-apparatus variability as well as variability due to degree of crystallinity, preferred orientation, sample preparation and other factors known to those skilled in the art and should be taken as qualitative measure only.

A "predetermined amount" as used herein with regard to crystalline valbenazine ditosylate of the present invention refers to the initial amount of crystalline valbenazine ditosylate used for the preparation of a pharmaceutical composition.

The term "pharmaceutically effective amount" as used herein with regard to crystalline valbenazine ditosylate of the present invention encompasses an amount of crystalline valbenazine ditosylate, which achieves the desired therapeutic and/or prophylactic effect. The term "pharmaceutically effective amount" also refers to the amount of a compound that is sufficient to elicit the biological or medical response of a cell, tissue, system, animal, or human that is being sought by a researcher, veterinarian, medical doctor, or clinician.

As used herein, the term "physical form" refers to any crystalline and/or amorphous phase of a compound.

"Relative humidity" as used herein refers to the ratio of the partial pressure of water vapor to the equilibrium vapor pressure of water at the same temperature. Relative humidity depends on temperature and the pressure of the system of interest. Unless otherwise specified, the temperature is 25° C. and the pressure is 1013 mbar.

The term "about" as used herein means within 5%, more typically within 1% and most typically within 0.5% of the indicated value or range.

Where the term "comprising" is used in the present description and claims, it does not exclude other elements or steps. For the purpose of the present invention, the term "consisting of" is considered to be the preferred embodiment of the term "comprising". If hereinafter a group is defined as comprising at least a certain number of embodiments, this is also to be understood as disclosing a group which optionally consists only of these embodiments.

The term "consisting essentially of" with reference to the amount of the crystalline valbenazine ditosylate or hydrate thereof in a composition means that slight variabilities in the amount are to be taken into account. This term is also to be understood herein in that such a composition comprises at least 96 w-%, preferably 98 w-%, more preferably 99 w-%, and most preferably 99.9 w-% of the crystalline valbenazine ditosylate as defined above, in particular the crystalline hydrate of valbenazine ditosylate as defined above, based on the total weight of the composition.

The term "consisting essentially of" with reference to the amount of the crystalline valbenazine dihydrochloride in a composition means that slight variabilities in the amount are to be taken into account. This term is also to be understood herein in that such a composition comprises at least 96 weight %, preferably 98 weight %, more preferably 99 weight %, and most preferably 99.9 weight % of the crystalline valbenazine dihydrochloride of the present invention, based on the total weight of the composition.

DETAILED DESCRIPTION OF THE INVENTION

Figure 1:
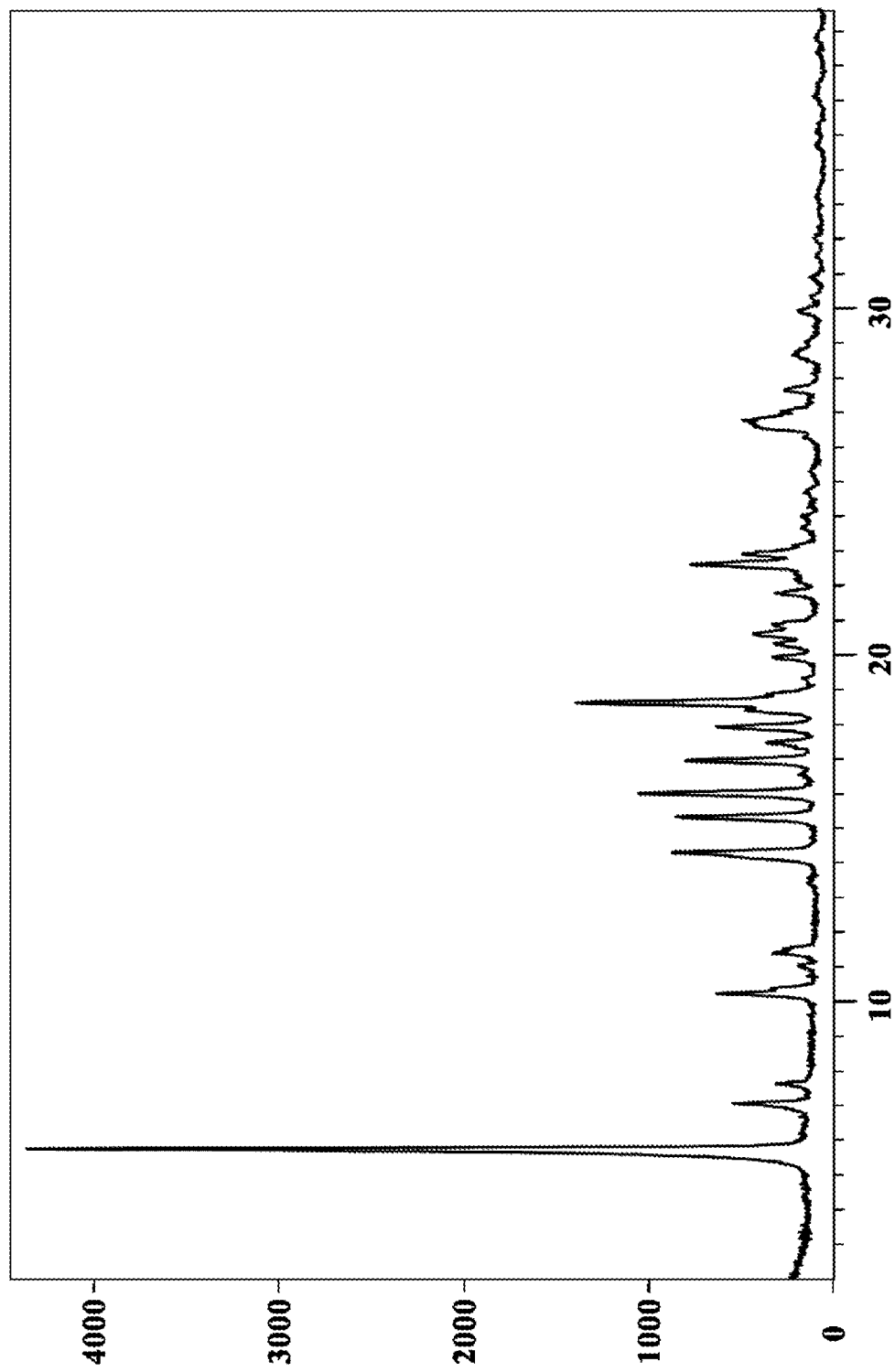
FIG. 1: illustrates a representative PXRD of the crystalline hydrate of valbenazine ditosylate according to the present invention. The x-axis shows the scattering angle in ° 2-theta, the y-axis shows the intensity of the scattered X-ray beam in counts of detected photons.

The present invention provides valbenazine ditosylate in crystalline form, preferably in form of a crystalline hydrate or in form of a crystalline anhydrate, which have one or more desirable properties, in particular compared to other solid forms of valbenazine rendering them especially suitable for the manufacture of a tablet formulation. In particular, the advantageous properties can be selected from the group consisting of chemical purity, solubility, dissolution rate, crystal morphology, polymorphic stability, thermal stability, mechanical stability, storage stability, a low content of residual solvent, a low degree of hygroscopicity, and advantageous processing and handling characteristics such as flowability, wettability, compressibility and bulk density.

Different aspects of the invention are described below in further detail by embodiments, without being limited thereto. Each aspect of the invention may be described by one embodiment or by combining two or more of the embodiments.

In one aspect, the present invention relates to crystalline valbenazine ditosylate characterized by the chemical structure according to Formula IV

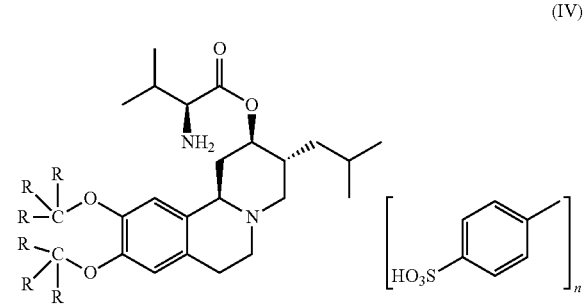

wherein:
each R is independently selected from H or D; and
n is in the range of from 1.7 to 2.3, preferably from 1.8 to 2.2, more preferably from 1.9 to 2.1 and most preferably n is 2.0.

In a preferred embodiment n is selected from the group consisting of 1.7, 1.8, 1.9, 2.0, 2.1, 2.2 and 2.3. In an embodiment at least one R is D. In an embodiment, all R are H. In another embodiment, all R are D.

In a preferred embodiment, the invention relates to a crystalline hydrate of valbenazine ditosylate characterized by the chemical structure according to Formula V

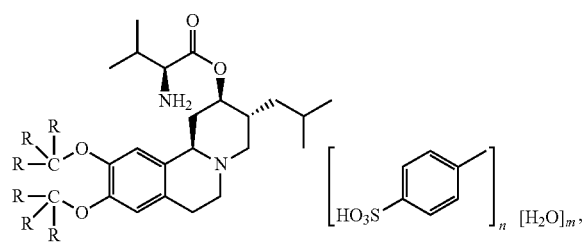
(V)

wherein:
each R is independently selected from H or D;
n is in the range of from 1.7 to 2.3, preferably from 1.8 to 2.2, more preferably from 1.9 to 2.1 and most preferably n is 2.0; and
m is in the range of from 0.1 to 4.0, preferably from 0.2 to 3.8, more preferably from 0.3 to 2.2 and most preferably from 0.5 to 1.6.

In a preferred embodiment n is selected from the group consisting of 1.7, 1.8, 1.9, 2.0, 2.1, 2.2 and 2.3. In an embodiment at least one R is D. In an embodiment, all R are H. In another embodiment, all R are D.

In one aspect, the present invention relates to crystalline valbenazine ditosylate characterized by the chemical structure according to Formula VI

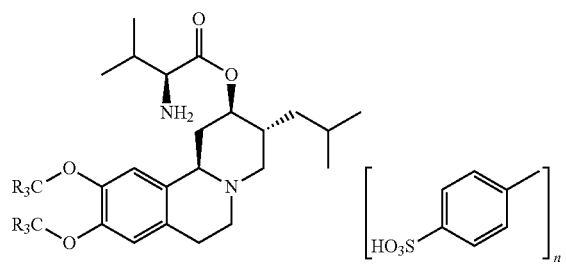
(VI)

wherein:
R is selected from H or D; and
n is in the range of from 1.7 to 2.3, preferably from 1.8 to 2.2, more preferably from 1.9 to 2.1 and most preferably n is 2.0.

In an embodiment R is H and n is selected from the group consisting of 1.7, 1.8, 1.9, 2.0, 2.1, 2.2 and 2.3. In another embodiment R is D and n is selected from the group consisting of 1.7, 1.8, 1.9, 2.0, 2.1, 2.2 and 2.3.

In a preferred embodiment, the invention relates to a crystalline hydrate of valbenazine ditosylate characterized by the chemical structure according to Formula VII

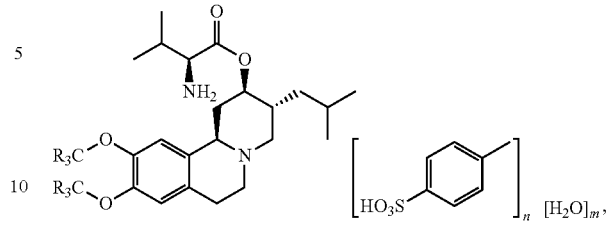
(VII)

wherein:
each R is independently selected from H or D;
n is in the range of from 1.7 to 2.3, preferably from 1.8 to 2.2, more preferably from 1.9 to 2.1 and most preferably n is 2.0; and
m is in the range of from 0.1 to 4.0, preferably from 0.2 to 3.8, more preferably from 0.3 to 2.2 and most preferably from 0.5 to 1.6.

In an embodiment R is H and n is selected from the group consisting of 1.7, 1.8, 1.9, 2.0, 2.1, 2.2 and 2.3. In another embodiment R is D and n is selected from the group consisting of 1.7, 1.8, 1.9, 2.0, 2.1, 2.2 and 2.3.

In one aspect, the present invention relates to crystalline valbenazine ditosylate characterized by the chemical structure according to Formula II

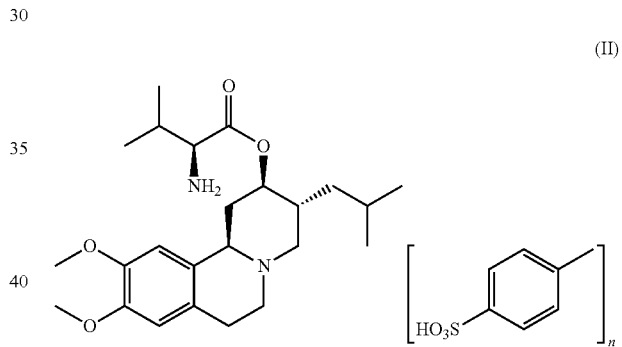
(II)

wherein n is in the range of from 1.7 to 2.3, preferably from 1.8 to 2.2, more preferably from 1.9 to 2.1 and most preferably n is 2.0. In one embodiment n is selected from the group consisting of 1.7, 1.8, 1.9, 2.0, 2.1, 2.2 and 2.3.

In a preferred embodiment, the invention relates to a crystalline hydrate of valbenazine ditosylate characterized by the chemical structure according to Formula III

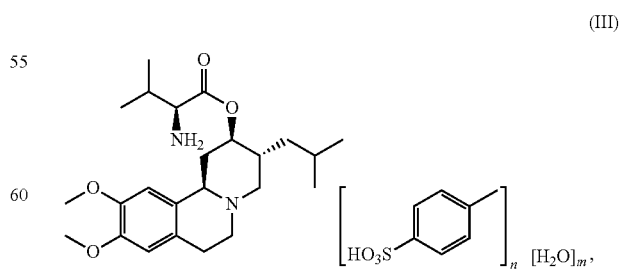
(III)

wherein n is in the range of from 1.7 to 2.3, preferably from 1.8 to 2.2, more preferably from 1.9 to 2.1 and most preferably n is 2.0 and m is in the range of from 0.1 to 4.0, preferably from 0.2 to 3.8, more preferably from 0.3 to 2.2 and most preferably from 0.5 to 1.6. In one embodiment n is selected from the group consisting of 1.7, 1.8, 1.9, 2.0, 2.1, 2.2 and 2.3.

Crystalline valbenazine ditosylate of the present invention may be characterized by analytical methods well known in the field of the pharmaceutical industry for characterizing solids. Such methods comprise but are not limited to PXRD, DSC, TGA and GMS. It may be characterized by one of the aforementioned analytical methods or by combining two or more of them. In particular, crystalline valbenazine ditosylate of the present invention may be characterized by any one of the following embodiments or by combining two or more of the following embodiments.

Crystalline Hydrate of Valbenazine Ditosylate

Hence, in one embodiment the present invention relates to crystalline valbenazine ditosylate, in particular to a crystalline hydrate of valbenazine ditosylate characterized by having a PXRD comprising reflections at 2-Theta angles of:
  $(5.7\pm0.2)°$, $(16.0\pm0.2)°$ and $(18.6\pm0.2)°$; or
  $(5.7\pm0.2)°$, $(14.3\pm0.2)°$, $(16.0\pm0.2)°$ and $(18.6\pm0.2)°$; or
  $(5.7\pm0.2)°$, $(10.2\pm0.2)°$, $(14.3\pm0.2)°$, $(16.0\pm0.2)°$ and $(18.6\pm0.2)°$; or
  $(5.7\pm0.2)°$, $(10.2\pm0.2)°$, $(14.3\pm0.2)°$, $(15.3\pm0.2)°$, $(16.0\pm0.2)°$ and $(18.6\pm0.2)°$; or
  $(5.7\pm0.2)°$, $(10.2\pm0.2)°$, $(14.3\pm0.2)°$, $(15.3\pm0.2)°$, $(16.0\pm0.2)°$, $(16.9\pm0.2)°$ and $(18.6\pm0.2)°$; or
  $(5.7\pm0.2)°$, $(7.1\pm0.2)°$, $(10.2\pm0.2)°$, $(14.3\pm0.2)°$, $(15.3\pm0.2)°$, $(16.0\pm0.2)°$, $(16.9\pm0.2)°$ and $(18.6\pm0.2)°$; or
  $(5.7\pm0.2)°$, $(7.1\pm0.2)°$, $(10.2\pm0.2)°$, $(14.3\pm0.2)°$, $(15.3\pm0.2)°$, $(16.0\pm0.2)°$, $(16.9\pm0.2)°$, $(17.9\pm0.2)°$ and $(18.6\pm0.2)°$; or
  $(5.7\pm0.2)°$, $(7.1\pm0.2)°$, $(10.2\pm0.2)°$, $(14.3\pm0.2)°$, $(15.3\pm0.2)°$, $(16.0\pm0.2)°$, $(16.9\pm0.2)°$, $(17.9\pm0.2)°$, $(18.6\pm0.2)°$ and $(22.6\pm0.2)°$;
  when measured at RT with Cu-Kalpha1,2 radiation having a wavelength of 0.15419 nm.

In another embodiment the present invention relates to crystalline valbenazine ditosylate, in particular to a crystalline hydrate of valbenazine ditosylate characterized by having a PXRD comprising reflections at 2-Theta angles of:
  $(5.7\pm0.1)°$, $(16.0\pm0.1)°$ and $(18.6\pm0.1)°$; or
  $(5.7\pm0.1)°$, $(14.3\pm0.1)°$, $(16.0\pm0.1)°$ and $(18.6\pm0.1)°$; or
  $(5.7\pm0.1)°$, $(10.2\pm0.1)°$, $(14.3\pm0.1)°$, $(16.0\pm0.1)°$ and $(18.6\pm0.1)°$; or
  $(5.7\pm0.1)°$, $(10.2\pm0.1)°$, $(14.3\pm0.1)°$, $(15.3\pm0.1)°$, $(16.0\pm0.1)°$ and $(18.6\pm0.1)°$; or
  $(5.7\pm0.1)°$, $(10.2\pm0.1)°$, $(14.3\pm0.1)°$, $(15.3\pm0.1)°$, $(16.0\pm0.1)°$, $(16.9\pm0.1)°$ and $(18.6\pm0.1)°$; or
  $(5.7\pm0.1)°$, $(7.1\pm0.1)°$, $(10.2\pm0.1)°$, $(14.3\pm0.1)°$, $(15.3\pm0.1)°$, $(16.0\pm0.1)°$, $(16.9\pm0.1)°$ and $(18.6\pm0.1)°$; or
  $(5.7\pm0.1)°$, $(7.1\pm0.1)°$, $(10.2\pm0.1)°$, $(14.3\pm0.1)°$, $(15.3\pm0.1)°$, $(16.0\pm0.1)°$, $(16.9\pm0.1)°$, $(17.9\pm0.1)°$ and $(18.6\pm0.1)°$; or
  $(5.7\pm0.1)°$, $(7.1\pm0.1)°$, $(10.2\pm0.1)°$, $(14.3\pm0.1)°$, $(15.3\pm0.1)°$, $(16.0\pm0.1)°$, $(16.9\pm0.1)°$, $(17.9\pm0.1)°$, $(18.6\pm0.1)°$ and $(22.6\pm0.1)°$;
  when measured at RT with Cu-Kalpha1,2 radiation having a wavelength of 0.15419 nm.

In another embodiment, the present invention relates to crystalline valbenazine ditosylate, in particular to a crystalline hydrate of valbenazine ditosylate characterized by having a PXRD essentially the same as shown in FIG. 1 of the present invention, when measured at RT with Cu-Kalpha1,2 radiation having a wavelength of 0.15419 nm.

In a further embodiment, the invention relates to crystalline valbenazine ditosylate, in particular to a crystalline hydrate of valbenazine ditosylate characterized by having a DSC curve comprising an endothermic peak with an onset temperature of about 131° C. and a peak temperature of about 148° C., when measured at a heating rate of 10 K/min.

In a preferred embodiment, the invention relates to crystalline valbenazine ditosylate, in particular a crystalline hydrate of valbenazine ditosylate characterized by having a DSC curve comprising an endothermic peak with an onset temperature of about $(131\pm2)°$ C. and a peak temperature of about $(148\pm2)°$ C., when measured at a heating rate of 10 K/min.

In a particular preferred embodiment, the invention relates to crystalline valbenazine ditosylate, in particular a crystalline hydrate of valbenazine ditosylate characterized by having a DSC curve comprising an endothermic peak with an onset temperature of about $(131\pm1)°$ C. and a peak temperature of about $(148\pm1)°$ C., when measured at a heating rate of 10 K/min.

The DSC data provided in Example 2 and FIG. 2 hereinafter proof that the crystalline hydrate of the present invention is very stable against temperature stress, since the first endotherm, which can be assigned to the dehydration event, only occurs well above 100° C. Hence, the hydrate of valbenazine ditosylate of the present invention possesses sufficient thermal stability for being formulated into a tablet such as a film-coated tablet, where significant temperature stress is for example generated during the coating process.

In a further embodiment, the present invention relates to crystalline valbenazine ditosylate, in particular to a crystalline hydrate of valbenazine ditosylate characterized by exhibiting a mass change of at most 5.0 w-%, preferably of at most 4.9 w-%, based on the weight of the crystalline valbenazine ditosylate, when measured with GMS at a RH in the range of from 5 to 80% and a temperature of $(25.0\pm0.1)°$ C.

In still a further embodiment, the present invention relates to crystalline valbenazine ditosylate, in particular to a crystalline hydrate of valbenazine ditosylate characterized by exhibiting a mass change of at most 3.0 w-%, preferably of at most 2.8 w-%, based on the weight of the crystalline valbenazine ditosylate, when measured with GMS at a RH in the range of from 20 to 70% and a temperature of $(25.0\pm0.1)°$ C.

In a preferred embodiment, the present invention relates to crystalline valbenazine ditosylate, in particular to a crystalline hydrate of valbenazine ditosylate characterized by exhibiting a mass change of at most 2.0 w-%, preferably of at most 1.9 w-%, based on the weight of the crystalline valbenazine ditosylate, when measured with GMS at a RH in the range of from 20 to 60% and a temperature of $(25.0\pm0.1)°$ C.

In a particular preferred embodiment, the present invention relates to crystalline valbenazine ditosylate, in particular a crystalline hydrate of valbenazine ditosylate characterized by exhibiting a mass change of at most 1.5 w-%, preferably of at most 1.3 w-%, based on the weight of the crystalline valbenazine ditosylate, when measured with GMS at a RH in the range of from 25 to 55% and a temperature of $(25.0\pm0.1)°$ C.

Figure 3:
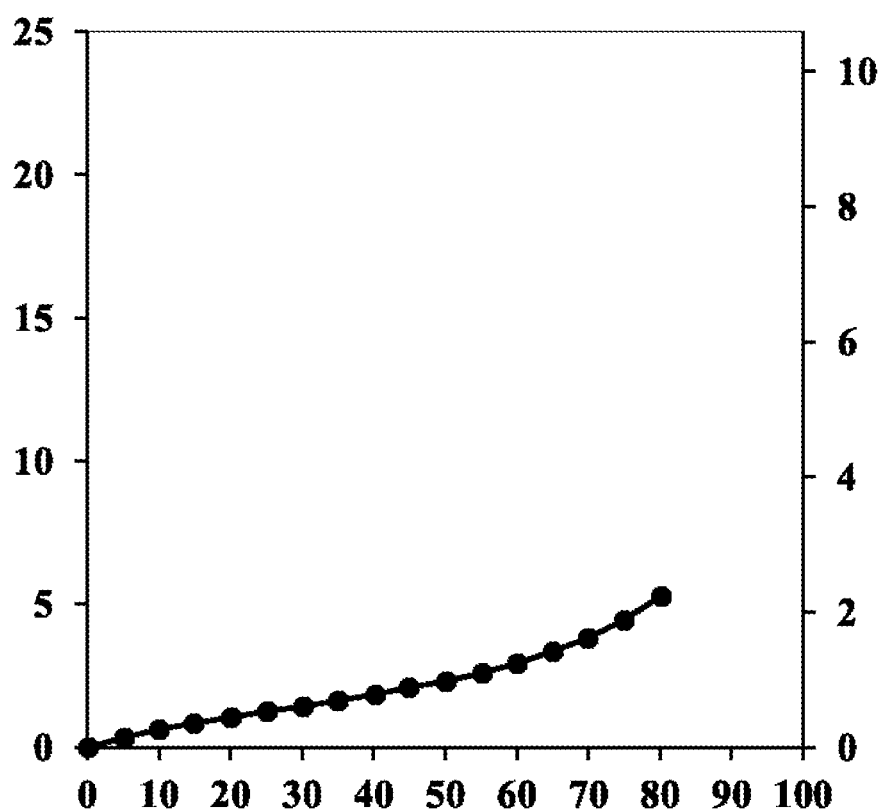
FIG. 3: illustrates a representative gravimetric moisture sorption curve of the crystalline hydrate of valbenazine ditosylate according to the present invention in the range of from 0 to 80% relative humidity. The x-axis displays the relative humidity in percent (%) measured at a temperature of (25.0±0.1)° C., the left y-axis displays the equilibrium mass change in weight percent (w-%) and the right y-axes displays the amount of water in mol per mol valbenazine ditosylate. The values are displayed as uncorrected values, whereat the weight at 0% relative humidity has been set to zero as starting weight.

As can be seen from the GMS curve displayed in FIG. 3 the hydrate of valbenazine ditosylate of the present invention does not require special precautionary measures during the tableting process, since no excessive weight gain or even deliquescence occur in the range of 0 to 80% relative humidity.

In a further aspect, the invention relates to a process for the preparation of crystalline valbenazine ditosylate, in particular the crystalline hydrate of valbenazine ditosylate as defined above or the composition comprising the same as defined hereinafter comprising:
(i) reacting valbenazine with p-toluenesulfonic acid monohydrate in toluene; and
(ii) removing toluene from the reaction mixture of step (i); and
(iii) optionally, drying the crystals obtained in step (ii).

Valbenazine, which is used as starting material in step (i) of the above described process may be prepared according to the process described in Example 2 of WO 2008/058261 A1 (compound 2-1) and p-toluenesulfonic acid monohydrate is commercially available.

Alternatively, deuterated valbenazine is used as starting material in step (i) of the above described process. This compound is e.g. disclosed in WO 2014/120654 and can be prepared according to the methods disclosed therein. In general, deuterated valbenazine can be produced by providing tetrabenazine or deutetrabenazine (WO 2010/044981, WO 2011/153157, WO 2015/084622) followed by reduction of the ketone to the corresponding alcohol, conjugation with N-protected L-valine and final removal of the N-protecting group.

Alternatively, deuterated valbenazine can be accessed starting from (+)-tetrabenazine via selective removal of the methoxy group under acidic conditions (see Brossi et al. Helvetica Chimica Acta (1958), 16, p. 119f) followed by alkylation with a deuterated methylating agent such as D3Cl or (D3CO)2SO2, followed by the final assembly.

Salt formation in step (i) is carried out in toluene, whereat 1.0 mol equivalent valbenazine is reacted with 1.7 to 2.3 mol equivalent, preferably with 1.8 to 2.2 mol equivalent, more preferably with 1.9 to 2.1 mol equivalent and most preferably with is 2.0 mol equivalent, p-toluenesulfonic acid. In a preferred embodiment, 1.0 mol equivalent valbenazine is reacted with 1.7, 1.8, 1.9, 2.0, 2.1, 2.2 or 2.3 mol equivalent p-toluene sulfonic acid. Preferably, p-toluene sulfonic acid is used in form of a monohydrate. The final valbenazine ditosylate concentration of the reaction mixture obtained in step (i) is preferably in the range of from 20 to 50 g/L, more preferably from 30 to 40 g/L.

The mixture obtained in step (i) is optionally slurried, wherein slurrying in the context of the present invention relates to any motion of the mixture comprising valbenazine ditosylate, which is caused by stirring, shaking and/or ultrasonic irradiation. Slurrying is performed at a temperature in the range of from about 20 to 100° C., preferably from about 20 to 80° C., more preferably from about 20 to 60° C., even more preferably from about 20 to 40° C. and most preferably slurrying is performed at about RT. Slurrying is performed for a period in the range of from about 6 to 48 hours, preferably from about 12 to 36 hours.

The crystalline hydrate is obtained by removing toluene in step (ii) of the above defined process. Toluene may be removed at atmospheric or at reduced pressure for example at a pressure of at most 500 mbar, more preferably of at most 100 mbar and most preferably of at most 50 mbar. In addition, toluene may be removed at RT or at elevated temperature for example at a temperature in the range of from about 20 to 100° C., preferably from about 20 to 80° C.; more preferably from about 20 to 60° C. and most preferably from about 20 to 40° C. In a preferred embodiment, toluene is removed by applying a vacuum of about 30 mbar and a temperature of about 40° C.

Finally, the obtained crystals may optionally be dried. Drying may be performed at a temperature of about 80° C. or less, preferably of about 60° C. or less, more preferably of about 40° C. or less and most preferably the crystals are dried at RT. Drying may be performed for a period in the range of from about 1 to 72 hours, preferably from about 2 to 48 hours, more preferably from about 4 to 24 hours and most preferably from about 6 to 18 hours. Drying may be performed at ambient pressure and/or under vacuum preferably at about 100 mbar or less, more preferably at about 50 mbar or less and most preferably at about 30 mbar or less, for example at about 20 mbar or less.

Crystalline Anhydrate of Valbenazine Ditosylate

In another embodiment, the present invention relates to crystalline valbenazine ditosylate, in particular to a crystalline anhydrate of valbenazine ditosylate characterized by having a PXRD comprising reflections at 2-Theta angles of:
  (6.3±0.2)°, (17.9±0.2)° and (19.8±0.2)°; or (6.3±0.2)°, (15.6±0.2)°, (17.9±0.2)° and (19.8±0.2)°; or
  (5.3±0.2)°, (6.3±0.2)°, (15.6±0.2)°, (17.9±0.2)° and (19.8±0.2)°; or
  (5.3±0.2)°, (6.3±0.2)°, (15.6±0.2)°, (16.6±0.2)°, (17.9±0.2)° and (19.8±0.2)°; or
  (5.3±0.2)°, (6.3±0.2)°, (12.6±0.2)°, (15.6±0.2)°, (16.6±0.2)°, (17.9±0.2)° and (19.8±0.2)°; or
  (5.3±0.2)°, (6.3±0.2)°, (12.6±0.2)°, (12.8±0.2)°, (15.6±0.2)°, (16.6±0.2)°, (17.9±0.2)° and (19.8±0.2)°;
  when measured at RT with Cu-Kalpha1,2 radiation having a wavelength of 0.15419 nm.

In another embodiment, the present invention relates to crystalline valbenazine ditosylate, in particular to a crystalline anhydrate of valbenazine ditosylate characterized by having a PXRD comprising reflections at 2-Theta angles of:
  (6.3±0.1)°, (17.9±0.1)° and (19.8±0.1)°; or
  (6.3±0.1)°, (15.6±0.1)°, (17.9±0.1)° and (19.8±0.1)°; or
  (5.3±0.1)°, (6.3±0.1)°, (15.6±0.1)°, (17.9±0.1)° and (19.8±0.1)°; or
  (5.3±0.1)°, (6.3±0.1)°, (15.6±0.1)°, (16.6±0.1)°, (17.9±0.1)° and (19.8±0.1)°; or
  (5.3±0.1)°, (6.3±0.1)°, (12.6±0.1)°, (15.6±0.1)°, (16.6±0.1)°, (17.9±0.1)° and (19.8±0.1)°; or
  (5.3±0.1)°, (6.3±0.1)°, (12.6±0.1)°, (12.8±0.1)°, (15.6±0.1)°, (16.6±0.1)°, (17.9±0.1)° and (19.8±0.1)°;
  when measured at RT with Cu-Kalpha1,2 radiation having a wavelength of 0.15419 nm.

Figure 4:
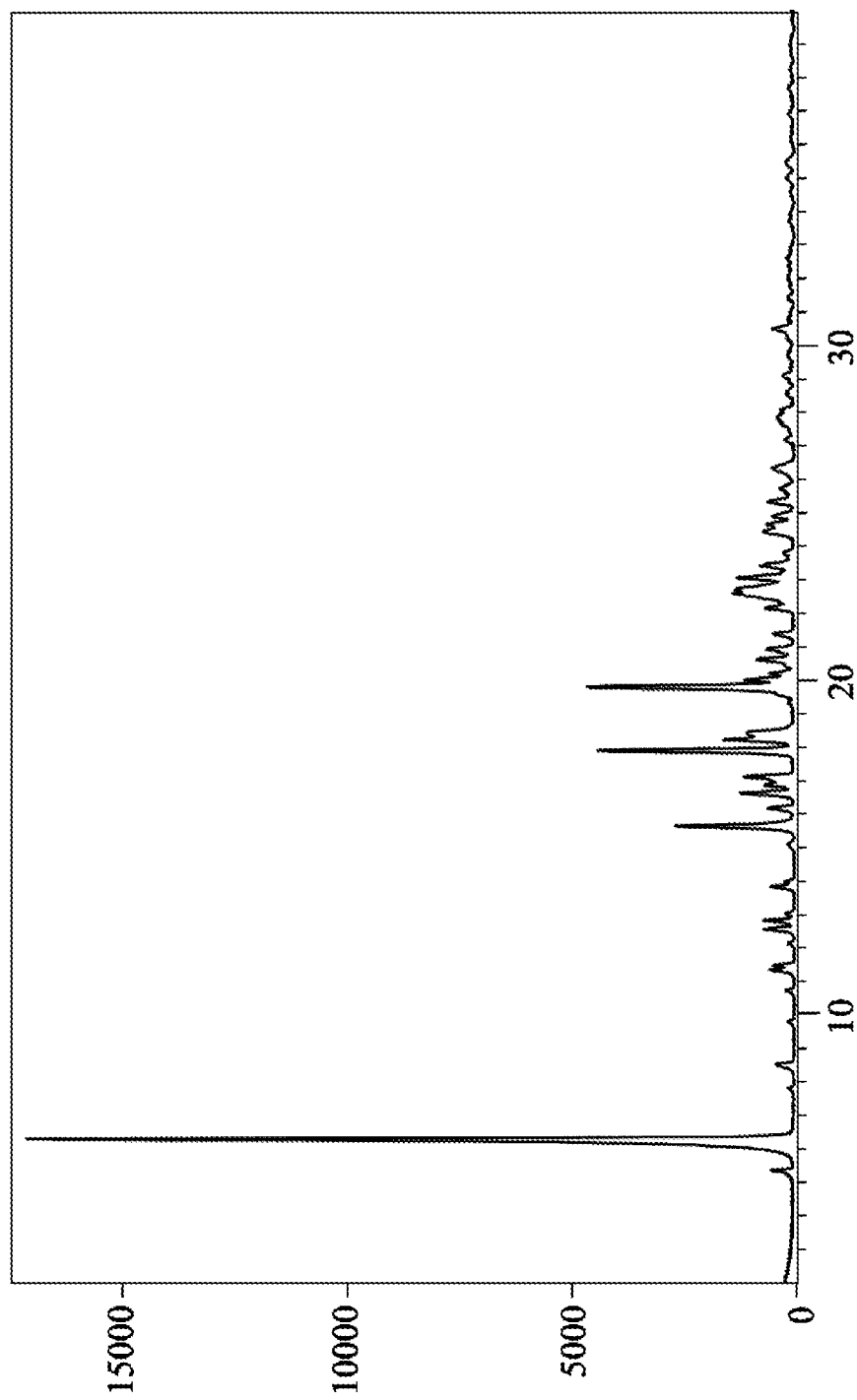
FIG. 4: illustrates a representative PXRD of the crystalline anhydrate of valbenazine ditosylate according to the present invention. The x-axis shows the scattering angle in ° 2-theta, the y-axis shows the intensity of the scattered X-ray beam in counts of detected photons.

In another embodiment, the present invention relates to crystalline valbenazine ditosylate, in particular to a crystalline anhydrate of valbenazine ditosylate characterized by having a PXRD essentially the same as shown in FIG. 4 of the present invention, when measured at RT with Cu-Kalpha1,2 radiation having a wavelength of 0.15419 nm.

In a further embodiment, the invention relates to crystalline valbenazine ditosylate, in particular to a crystalline anhydrate of valbenazine ditosylate characterized by having a DSC curve comprising an endothermic peak with an onset temperature of about 239° C. and a peak temperature of about 242° C., when measured at a heating rate of 10 K/min.

In a preferred embodiment, the invention relates to crystalline valbenazine ditosylate, in particular a crystalline anhydrate of valbenazine ditosylate characterized by having a DSC curve comprising an endothermic peak with an onset temperature of about (239±2)° C. and a peak temperature of about (242±2)° C., when measured at a heating rate of 10 K/min.

In a particular preferred embodiment, the invention relates to crystalline valbenazine ditosylate, in particular a crystalline anhydrate of valbenazine ditosylate characterized by having a DSC curve comprising an endothermic peak with an onset temperature of about (239±1)° C. and a peak temperature of about (242±1)° C., when measured at a heating rate of 10 K/min.

The DSC data provided in Example 7 and FIG. 5 hereinafter proof that the crystalline anhydrate of the present invention is very stable against temperature stress, since the first and only endotherm, which can be assigned to the melting event, only occurs at about 239° C. Hence, the anhydrate of valbenazine ditosylate of the present invention possesses sufficient thermal stability for being formulated into a tablet such as a film-coated tablet, where significant temperature stress is for example generated during the coating process.

In another embodiment, the present invention relates to crystalline valbenazine ditosylate, in particular a crystalline anhydrate of valbenazine ditosylate characterized by having a TGA curve showing a mass loss of not more than 1.0 w-%, preferably of not more than 0.5 w-%, more preferably of not more than 0.3 w-%, based on the weight of the crystalline form, when measured in the temperature range of from 25 to 140° C. at a heating rate of 10 K/min.

Figure 6:
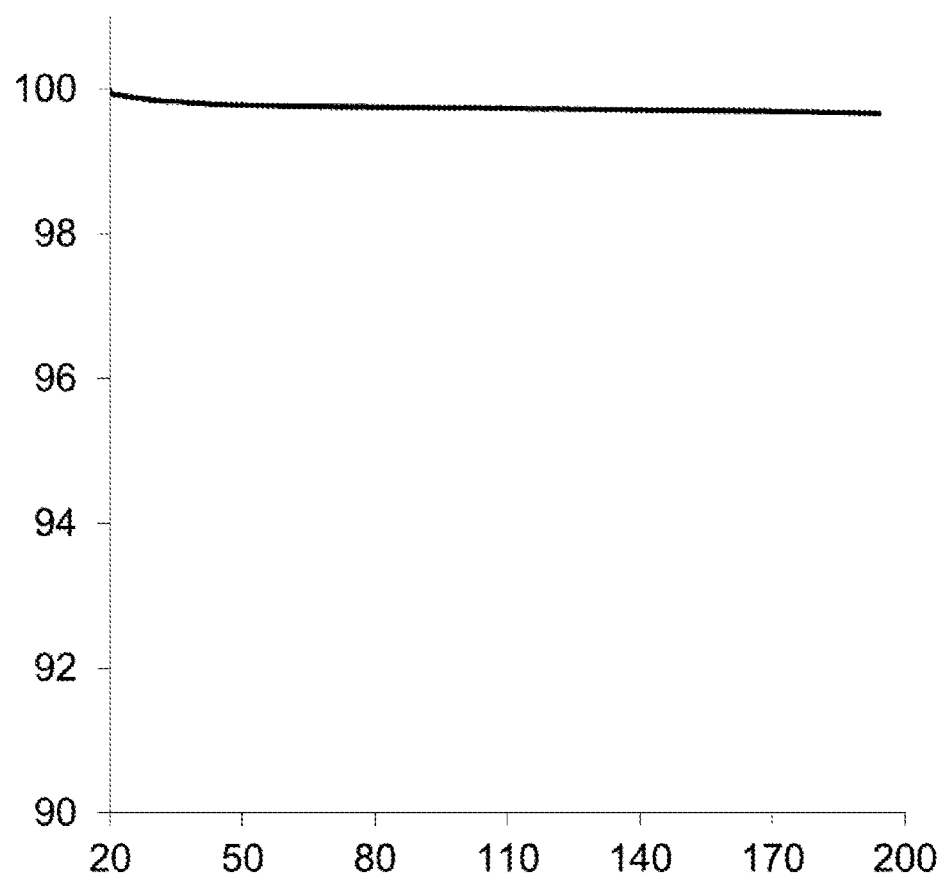
FIG. 6: illustrates a representative thermogravimetric analysis (TGA) curve of the crystalline anhydrate of valbenazine ditosylate according to the present invention. The x-axis shows the temperature in degree Celsius (° C.), the y-axis shows the mass (loss) of the sample in weight percent (w-%).

TGA further confirmed the thermal stability of the crystalline anhydrate of valbenazine ditosylate of the present invention. As can be seen from the data provided in Example 8 and FIG. 6 hereinafter, no significant weight loss can be observed in the course of the TGA experiment up to a temperature of about 200° C.

In still another aspect the invention relates to a process for the preparation of crystalline valbenazine ditosylate, in particular the crystalline anhydrate of valbenazine ditosylate as defined above or the composition comprising the same as defined hereinafter comprising:
 (i) reacting valbenazine with p-toluenesulfonic acid monohydrate in a solvent selected from the group consisting of ethers, nitriles and esters or mixtures thereof; and
 (ii) separating at least a part of the obtained crystals from the reaction mixture of step (i); and
 (iii) optionally, drying the crystals obtained in step (ii).

Valbenazine, which is used as starting material in step (i) of the above described process may be prepared according to the process described in Example 2 of WO 2008/058261 A1 (compound 2-1) and p-toluenesulfonic acid monohydrate is commercially available.

Alternatively, deuterated valbenazine is used as starting material in step (i) of the above described process. This compound is e.g. disclosed in WO 2014/120654 and can be prepared according to the methods disclosed therein. In general, deuterated valbenazine can be produced by providing tetrabenazine or deutetrabenazine (WO 2010/044981, WO 2011/153157, WO 2015/084622) followed by reduction of the ketone to the corresponding alcohol, conjugation with N-protected L-valine and final removal of the N-protecting group. Alternatively, deuterated valbenazine can be accessed starting from (+)-tetrabenazine via selective removal of the methoxy group under acidic conditions (see Brossi et al. Helvetica Chimica Acta (1958), 16, p. 119f) followed by alkylation with a deuterated methylating agent such as D3Cl or (D3CO)2SO2, followed by the final assembly.

Salt formation in step (i) is carried out in a solvent selected from the group consisting of ethers, nitriles and esters or mixtures thereof. A suitable ether is for example diethyl ether, a suitable nitrile is for example acetonitrile and a suitable ester, which may be applied is for example butyl acetate. The reaction is carried out by reacting 1.0 mol equivalent valbenazine with 1.7 to 2.3 mol equivalent, preferably with 1.8 to 2.2 mol equivalent, more preferably with 1.9 to 2.1 mol equivalent and most preferably with is 2.0 mol equivalent, p-toluenesulfonic acid. In a preferred embodiment, 1.0 mol equivalent valbenazine is reacted with 1.7, 1.8, 1.9, 2.0, 2.1, 2.2 or 2.3 mol equivalent p-toluene sulfonic acid. Preferably, p-toluene sulfonic acid is used in form of a monohydrate. The final valbenazine ditosylate concentration of the reaction mixture obtained in step (i) is preferably in the range of from 20 to 50 g/L, more preferably from 30 to 40 g/L.

The mixture obtained in step (i) is optionally slurried, wherein slurrying in the context of the present invention relates to any motion of the mixture comprising valbenazine ditosylate, which is caused by stirring, shaking and/or ultrasonic irradiation. Slurrying is performed at a temperature in the range of from about 20 to 100° C., preferably from about 20 to 80° C., more preferably from about 20 to 60° C., even more preferably from about 20 to 40° C. and most preferably slurrying is performed at about RT. Slurrying is performed for a period in the range of from about 6 to 48 hours, preferably from about 6 to 24 hours, such as about 12 hours.

The crystalline anhydrate or at least a part thereof is separated from the reaction mixture by any conventional methods such as filtration, centrifugation or solvent evaporation, preferably by filtration.

Finally, the obtained crystals may optionally be dried. Drying may be performed at a temperature of about 80° C. or less, preferably of about 60° C. or less, more preferably of about 40° C. or less and most preferably the crystals are dried at RT. Drying may be performed for a period in the range of from about 1 to 72 hours, preferably from about 2 to 48 hours, more preferably from about 4 to 24 hours and most preferably from about 6 to 18 hours. Drying may be performed at ambient pressure and/or under vacuum preferably at about 100 mbar or less, more preferably at about 50 mbar or less and most preferably at about 30 mbar or less, for example at about 20 mbar or less.

Composition Comprising Crystalline Valbenazine Ditosylate

In another aspect, the invention relates to a composition comprising the crystalline valbenazine ditosylate as defined above, in particular the crystalline hydrate or anhydrate of valbenazine ditosylate as defined above, which composition is essentially free of any other physical form of valbenazine ditosylate.

In a preferred embodiment, the invention relates to a composition comprising the crystalline valbenazine ditosylate as defined above, in particular the crystalline hydrate or anhydrate of valbenazine ditosylate as defined above, characterized by comprising at most 20 w-%, preferably at most 10 w-%, more preferably at most 5 w-%, even more preferably at most 2 w-% and most preferably at most 1 w-% of any other physical form of valbenazine ditosylate, based on the total weight of the composition. In a particular preferred embodiment, the any other physical form is amorphous valbenazine ditosylate.

In another embodiment, the invention relates to a composition comprising at least 90 w-% of the crystalline valbenazine ditosylate as defined above, in particular the crystalline hydrate or anhydrate of valbenazine ditosylate as defined above, based on the total weight of the composition. Preferably, the composition comprises less than 5 w-% amorphous valbenazine ditosylate, such as less than 2 w-% amorphous valbenazine ditosylate.

In a further embodiment, the invention relates to a composition comprising at least 95 w-% of the crystalline valbenazine ditosylate as defined above, in particular the crystalline hydrate or anhydrate of valbenazine ditosylate as defined above, based on the total weight of the composition. Preferably, the composition comprises less than 4 w-% amorphous valbenazine ditosylate, such as less than 2 w-% amorphous valbenazine ditosylate.

In a preferred embodiment, the invention relates to a composition consisting essentially of the crystalline valbenazine ditosylate as defined above. In another preferred embodiment, the invention relates to a composition consisting essentially of the crystalline anhydrate of valbenazine ditosylate according to Formula II as defined above, wherein n is 2.0. In another preferred embodiment, the invention relates to a composition consisting essentially of the hydrate of the crystalline valbenazine ditosylate according to Formula III as defined above, wherein n is 2.0 and m is in the range of from 0.1 to 4.0, preferably from 0.2 to 3.8, more preferably from 0.3 to 2.2 and most preferably from 0.5 to 1.6.

Valbenazine Dihydrochloride

In a further aspect the present invention provides crystalline valbenazine dihydrochloride. In particular, the present invention relates to crystalline forms of valbenazine dihydrochloride, which have one or more desirable properties, compared to other solid forms of valbenazine rendering them especially suitable for the manufacture of a tablet formulation. In particular, the advantageous properties can be selected from the group consisting of chemical purity, solubility, dissolution rate, crystal morphology, polymorphic stability, thermal stability, mechanical stability, storage stability, a low content of residual solvent, a low degree of hygroscopicity, and advantageous processing and handling characteristics such as flowability, wettability, compressibility and bulk density.

Different aspects of the invention are described below in further detail by embodiments, without being limited thereto. Each aspect of the invention may be described by one embodiment or by combining two or more of the embodiments.

In one aspect, the present invention relates to crystalline valbenazine dihydrochloride characterized by the chemical structure according to Formula (IX)

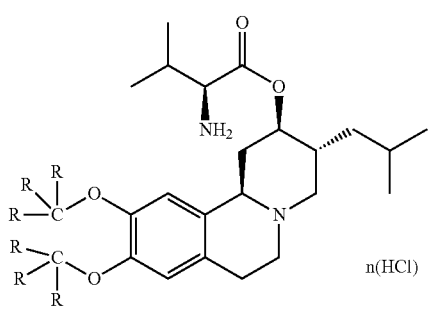

(IX)

wherein:

each R is independently selected from H or D; and n is in the range of from 1.7 to 2.3, preferably from 1.8 to 2.2, more preferably from 1.9 to 2.1 and most preferably n is 2.0.

In a preferred embodiment n is selected from the group consisting of 1.7, 1.8, 1.9, 2.0, 2.1, 2.2 and 2.3. In an embodiment at least one R is D. In an embodiment, all R are H. In another embodiment, all R are D.

In one aspect, the present invention relates to crystalline valbenazine dihydrochloride characterized by the chemical structure according to Formula (X)

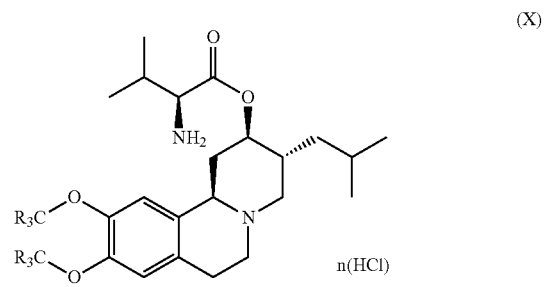

(X)

wherein:

R is selected from H or D; and n is in the range of from 1.7 to 2.3, preferably from 1.8 to 2.2, more preferably from 1.9 to 2.1 and most preferably n is 2.0.

In an embodiment R is H and n is selected from the group consisting of 1.7, 1.8, 1.9, 2.0, 2.1, 2.2 and 2.3. In another embodiment R is D and n is selected from the group consisting of 1.7, 1.8, 1.9, 2.0, 2.1, 2.2 and 2.3.

In one aspect, the present invention relates to crystalline valbenazine dihydrochloride characterized by the chemical structure according to Formula (VIII)

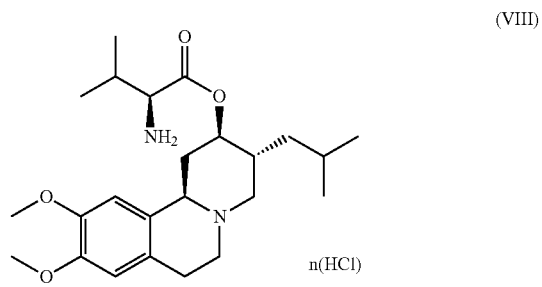

(VIII)

wherein n is in the range of from 1.7 to 2.3, preferably from 1.8 to 2.2, more preferably from 1.9 to 2.1 and most preferably n is 2.0. In one embodiment n is selected from the group consisting of 1.7, 1.8, 1.9, 2.0, 2.1, 2.2 and 2.3.

The First Crystalline Form of Valbenazine Dihydrochloride of the Present Invention The present invention relates to a crystalline form of valbenazine dihydrochloride of Formula (VIII), (IX) or (X), characterized by having a powder X-ray diffractogram comprising reflections at 2-Theta angles of:

(6.9±0.2)°, (7.2±0.2)° and (9.2±0.2)°; or (6.9±0.2)°, (7.2±0.2)°, (9.2±0.2)° and (12.7±0.2)°; or (6.9±0.2)°, (7.2±0.2)°, (9.2±0.2)°, (12.7±0.2)° and (18.1±0.2)°; or (6.9±0.2)°, (7.2±0.2)°, (9.2±0.2)°, (10.7±0.2)°, (12.7±0.2)° and (18.1±0.2)°; or (6.9±0.2)°, (7.2±0.2)°, (9.2±0.2)°, (10.7±0.2)°, (12.7±0.2)°, (14.1±0.2)° and (18.1±0.2)°; or (6.9±0.2)°, (7.2±0.2)°, (9.2±0.2)°, (10.7±0.2)°, (12.7±0.2)°, (14.1±0.2)°, (15.1±0.2)° and (18.1±0.2)°; or (6.9±0.2)°, (7.2±0.2)°, (9.2±0.2)°, (10.7±0.2)°, (12.7±0.2)°, (14.1±0.2)°, (15.1±0.2)°, (17.5±0.2)° and (18.1±0.2)°; or (6.9±0.2)°, (7.2±0.2)°, (9.2±0.2)°, (10.7±0.2)°, (12.7±0.2)°, (14.1±0.2)°, (15.1±0.2)°, (17.5±0.2)°, (18.1±0.2)° and (20.9±0.2)°;

when measured at a temperature in the range of from 20 to 30° C. with Cu-Kalpha1,2 radiation having a wavelength of 0.15419 nm.

In another embodiment, the present invention relates to a crystalline form of valbenazine dihydrochloride of Formula (VIII), (IX) or (X), characterized by having a powder X-ray diffractogram comprising reflections at 2-Theta angles of:
(6.9±0.1)°, (7.2±0.1)° and (9.2±0.1)°; or
(6.9±0.1)°, (7.2±0.1)°, (9.2±0.1)° and (12.7±0.1)°; or
(6.9±0.1)°, (7.2±0.1)°, (9.2±0.1)°, (12.7±0.1)° and (18.1±0.1)°; or
(6.9±0.1)°, (7.2±0.1)°, (9.2±0.1)°, (10.7±0.1)°, (12.7±0.1)° and (18.1±0.1)°; or
(6.9±0.1)°, (7.2±0.1)°, (9.2±0.1)°, (10.7±0.1)°, (12.7±0.1)°, (14.1±0.1)° and (18.1±0.1)°; or
(6.9±0.1)°, (7.2±0.1)°, (9.2±0.1)°, (10.7±0.1)°, (12.7±0.1)°, (14.1±0.1)°, (15.1±0.1)° and (18.1±0.1)°; or
(6.9±0.1)°, (7.2±0.1)°, (9.2±0.1)°, (10.7±0.1)°, (12.7±0.1)°, (14.1±0.1)°, (15.1±0.1)°, (17.5±0.1)° and (18.1±0.1)°; or
(6.9±0.1)°, (7.2±0.1)°, (9.2±0.1)°, (10.7±0.1)°, (12.7±0.1)°, (14.1±0.1)°, (15.1±0.1)°, (17.5±0.1)°, (18.1±0.1)° and (20.9±0.1)°;
when measured at a temperature in the range of from 20 to 30° C. with Cu-Kalpha1,2 radiation having a wavelength of 0.15419 nm.

Figure 7:
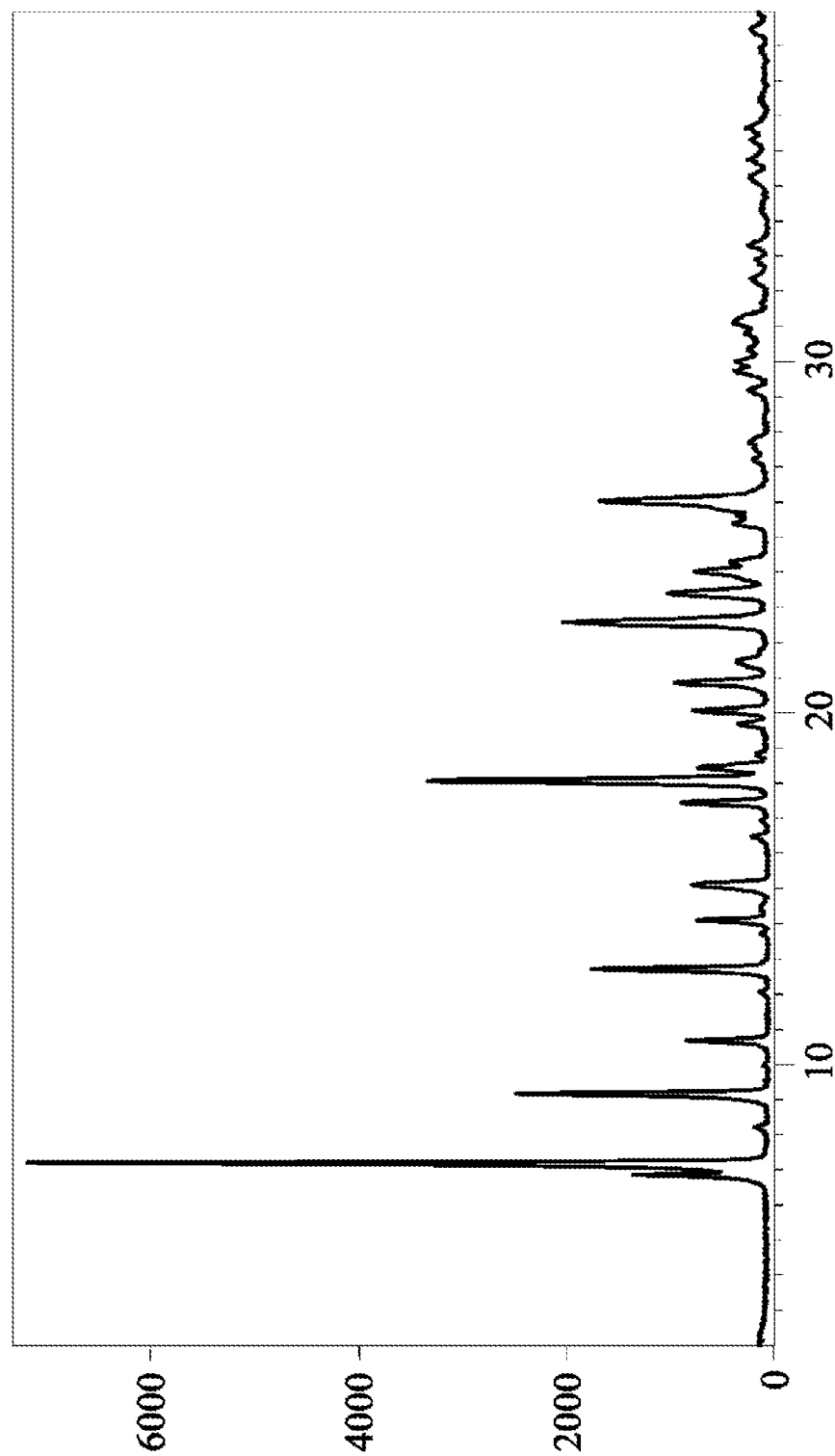
FIG. 7: illustrates a representative powder X-ray diffractogram of the first crystalline form of valbenazine dihydrochloride according to the present invention. The x-axis shows the scattering angle in ° 2-Theta, the y-axis shows the intensity of the scattered X-ray beam in counts of detected photons.

In another embodiment, the present invention relates to a crystalline form of valbenazine dihydrochloride of Formula (VIII), (IX) or (X), characterized by having a powder X-ray diffractogram essentially the same as shown in FIG. 7 of the present invention, when measured at a temperature in the range of from 20 to 30° C. with Cu-Kalpha1,2 radiation having a wavelength of 0.15419 nm.

In a further aspect, the invention relates to a process for the preparation of the first crystalline form of valbenazine dihydrochloride of Formula (VIII), (IX) or (X) as defined above comprising:
(i) providing a solution comprising valbenazine dihydrochloride and acetone; and
(ii) crystallizing valbenazine dihydrochloride from the solution provided in step (i); and
(iii) separating at least a part of the crystals obtained in step (ii) from the mother liquor; and
(iv) optionally, drying the crystals obtained in step (iii).

Valbenazine may be prepared according to the process described in Example 2 of WO 2008/058261 A1 (compound 2-1) and hydrochloric acid is commercially available. Alternatively, deuterated valbenazine is used. This compound is e.g. disclosed in WO 2014/120654 and can be prepared according to the methods disclosed therein. In general, deuterated valbenazine can be produced by providing tetrabenazine or deutetrabenazine (WO 2010/044981, WO 2011/153157, WO 2015/084622) followed by reduction of the ketone to the corresponding alcohol, conjugation with N-protected L-valine and final removal of the N-protecting group. Alternatively, deuterated valbenazine can be accessed starting from (+)-tetrabenazine via selective removal of the methoxy group under acidic conditions (see Brossi et al. Helvetica Chimica Acta (1958), 16, p. 119f) followed by alkylation with a deuterated methylating agent such as D3Cl or (D3CO)2SO2, followed by the final assembly.

Valbenazine dihydrochloride, which is used as starting material in step (i) of the above described process may be prepared by reacting valbenazine or deuterated valbenazine with hydrochloric acid in a suitable solvent. The valbenazine dihydrochloride starting material may be prepared according to the procedure provided in Example 16 herein, leading to amorphous material.

In step (i) a solution of valbenazine dihydrochloride in a solvent comprising acetone is prepared. Preferably, acetone is the only solvent present. The solution is preferably prepared by heating valbenazine dihydrochloride in acetone e.g. to a temperature in the range of from 30 to 56° C., preferably of from 40 to 56° C. and most preferably the solution is heated to reflux temperature. Once, a solution is obtained, it may optionally be filtrated in order to remove any undissolved particles. The final valbenazine dihydrochloride concentration of the solution obtained in step (i) is preferably in the range of from 5 to 20 g/L, more preferably of from 5 to 15 g/L, for example the final concentration is about 10 g/L.

In step (ii) of the above described process the valbenazine dihydrochloride is crystallized from the solution obtained in step (i). Thereby, crystallization may occur spontaneously by leaving the solution with or without slurrying, wherein slurrying in the context of the present invention relates to any motion of the mixture comprising valbenazine dihydrochloride, which is caused by stirring, shaking and/or ultrasonic irradiation. In order to accelerate the crystallization, the solution may be naturally or actively cooled to room temperature or a temperature in the range of from −10 to +20° C., for example of from 0 to 10° C. Crystallization may also be initiated by adding seed crystals to the solution. Seed crystals can be prepared according to Example 13 herein. The amount of seed crystals applied may range from 1 to 20 weight %, preferably from 2 to 5 weight %, based on the weight of the valbenazine dihydrochloride present in the solution.

Once, crystallization occurred the obtained suspension is optionally further kept at a temperature in the range of from −10 to +20° C., for example of from 0 to 10° C. to increase the yield before the valbenazine dihydrochloride crystals are separated from the mother liquor by any conventional method such as filtration or centrifugation, most preferably by filtration. Optionally, the isolated crystals may be washed with a solvent. Preferably, the solvent comprises acetone and most preferably, the solvent is acetone.

Finally, the valbenazine dihydrochloride crystals may optionally be dried at a temperature in the range of from 20 to 60° C., more preferably of from 20 to 40° C. and most preferably the crystals are dried at room temperature. Drying may be performed for a period of time in the range of from about 1 to 72 hours, preferably from about 2 to 48 hours, more preferably from about 4 to 24 hours and most preferably from about 6 to 18 hours. Drying may be performed at ambient pressure and/or under vacuum preferably at about 100 mbar or less, more preferably at about 50 mbar or less and most preferably at about 30 mbar or less.

The Second Crystalline Form of Valbenazine Dihydrochloride of the Present Invention The present invention relates to a crystalline form of valbenazine dihydrochloride of Formula (VIII), (IX) or (X) characterized by having a powder X-ray diffractogram comprising reflections at 2-Theta angles of:
(12.0±0.2)°, (16.3±0.2)° and (21.5±0.2)°; or
(12.0±0.2)°, (16.3±0.2)°, (20.5±0.2)° and (21.5±0.2)°; or
(12.0±0.2)°, (16.3±0.2)°, (18.8±0.2)°, (20.5±0.2)° and (21.5±0.2)°; or
(12.0±0.2)°, (16.3±0.2)°, (18.8±0.2)°, (19.1±0.2)°, (20.5±0.2)° and (21.5±0.2)°; or
(12.0±0.2)°, (16.3±0.2)°, (18.8±0.2)°, (19.1±0.2)°, (20.5±0.2)°, (21.5±0.2)° and (23.2±0.2)°;
when measured at a temperature in the range of from 20 to 30° C. with Cu-Kalpha1,2 radiation having a wavelength of 0.15419 nm. Preferably the powder X-ray diffractogram does not comprise a reflection at a 2-Theta angle of (7.2±0.1)°.

In another embodiment, the present invention relates to a crystalline form of valbenazine dihydrochloride of Formula (VIII), (IX) or (X), characterized by having a powder X-ray diffractogram comprising reflections at 2-Theta angles of:

(12.0±0.1)°, (16.3±0.1)° and (21.5±0.1)°; or
(12.0±0.1)°, (16.3±0.1)°, (20.5±0.1)° and (21.5±0.1)°; or
(12.0±0.1)°, (16.3±0.1)°, (18.8±0.1)°, (20.5±0.1)° and (21.5±0.1)°; or
(12.0±0.1)°, (16.3±0.1)°, (18.8±0.1)°, (19.1±0.1)°, (20.5±0.1)° and (21.5±0.1)°; or
(12.0±0.1)°, (16.3±0.1)°, (18.8±0.1)°, (19.1±0.1)°, (20.5±0.1)°, (21.5±0.1)° and (23.2±0.1)°;

when measured at a temperature in the range of from 20 to 30° C. with Cu-Kalpha1,2 radiation having a wavelength of 0.15419 nm. Preferably the powder X-ray diffractogram does not comprise a reflection at a 2-Theta angle of (7.2±0.1)°.

Figure 8:
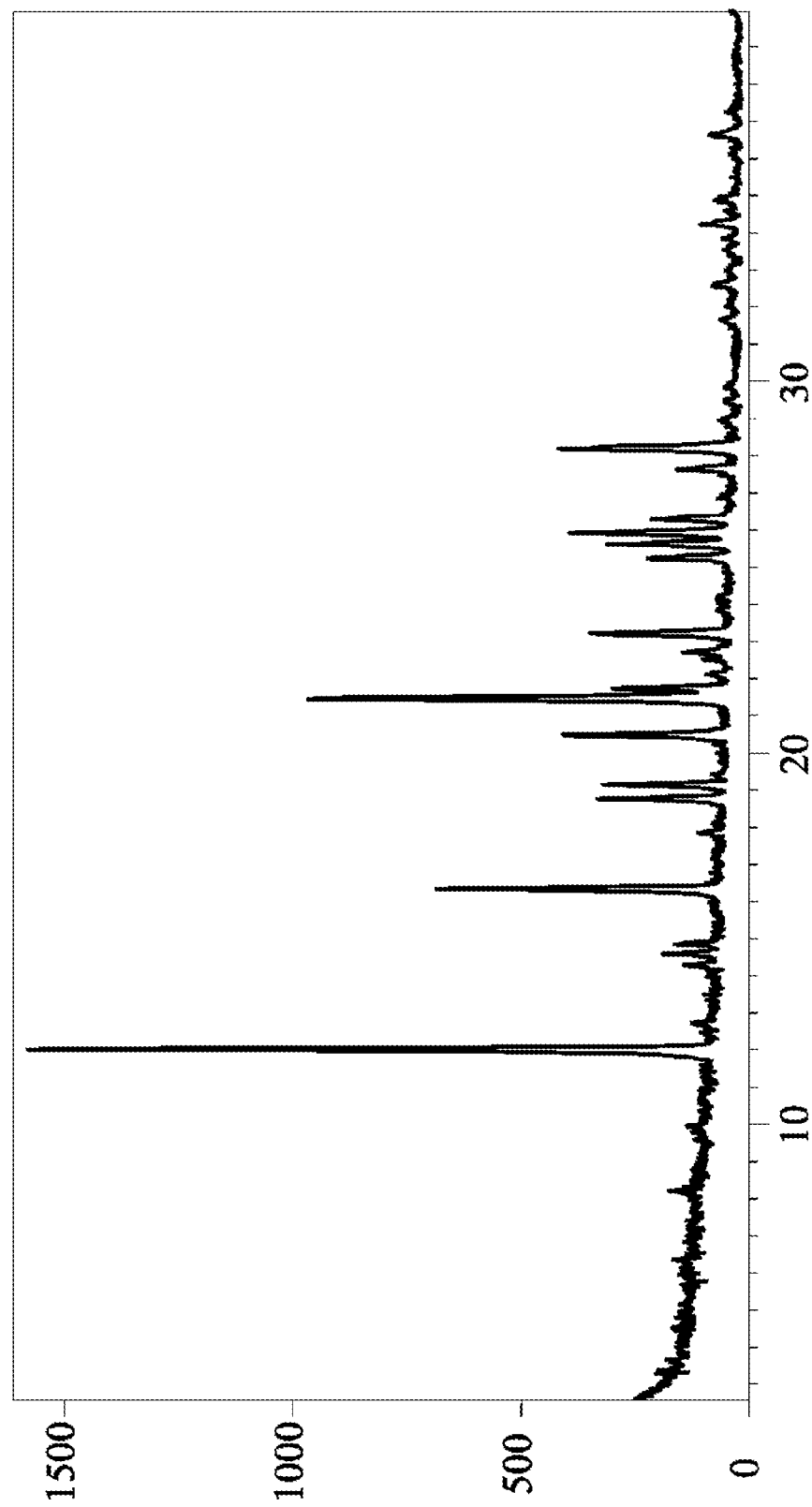
FIG. 8: illustrates a representative powder X-ray diffractogram of the second crystalline form of valbenazine dihydrochloride according to the present invention. The x-axis shows the scattering angle in ° 2-Theta, the y-axis shows the intensity of the scattered X-ray beam in counts of detected photons.

In another embodiment, the present invention relates to a crystalline form of valbenazine dihydrochloride of Formula (VIII), (IX) or (X), characterized by having a powder X-ray diffractogram essentially the same as shown in FIG. 8 of the present invention, when measured at a temperature in the range of from 20 to 30° C. with Cu-Kalpha1,2 radiation having a wavelength of 0.15419 nm.

In a further aspect, the invention relates to a process for the preparation of the second crystalline form of valbenazine dihydrochloride of Formula (VIII), (IX) or (X) as defined above comprising:

(a) providing a suspension comprising valbenazine dihydrochloride and acetone; and
(b) slurrying the suspension provided in step (a); and
(c) separating at least a part of the crystals obtained in step (b) from the mother liquor; and
(d) optionally, drying the crystals obtained in step (c).

Valbenazine may be prepared according to the process described in Example 2 of WO 2008/058261 A1 (compound 2-1) and hydrochloric acid is commercially available. Alternatively, deuterated valbenazine is used. This compound is e.g. disclosed in WO 2014/120654 and can be prepared according to the methods disclosed therein. In general, deuterated valbenazine can be produced by providing tetrabenazine or deutetrabenazine (WO 2010/044981, WO 2011/153157, WO 2015/084622) followed by reduction of the ketone to the corresponding alcohol, conjugation with N-protected L-valine and final removal of the N-protecting group. Alternatively, deuterated valbenazine can be accessed starting from (+)-tetrabenazine via selective removal of the methoxy group under acidic conditions (see Brossi et al. Helvetica Chimica Acta (1958), 16, p. 119f) followed by alkylation with a deuterated methylating agent such as D3Cl or (D3CO)2SO2, followed by the final assembly.

Valbenazine dihydrochloride, which is used as starting material in step (a) of the above described process may be prepared by reacting valbenazine or deuterated valbenazine with hydrochloric acid in a suitable solvent. The valbenazine dihydrochloride starting material may be prepared according to the procedure provided in Example 16 herein, leading to amorphous material.

In step (a) a suspension of valbenazine dihydrochloride in a solvent comprising acetone is prepared. Preferably, acetone is the only solvent present. The final valbenazine dihydrochloride concentration of the suspension obtained in step (a) is preferably in the range of from 30 to 70 g/L, more preferably of from 40 to 60 g/L, for example the final concentration is about 50 g/L. The suspension may be heated to a temperature in the range of from 30 to 50° C., preferably of from 35 to 45° C. and most preferably the suspension is heated to about 40° C.

In step (b) of the above described process the suspension is slurried, wherein slurrying in the context of the present invention relates to any motion of the mixture comprising valbenazine dihydrochloride, which is caused by stirring, shaking and/or ultrasonic irradiation. Preferably, the temperature of the suspension is kept in the range of from 30 to 50° C., preferably of from 35 to 45° C. and most preferably the temperature of the suspension is kept about 40° C. during slurrying. Slurrying is performed for a period in the range of from 6 to 48 hours, for example for about 10 hours.

In a next step, the crystals are separated from the mother liquor by any conventional method such as filtration or centrifugation, most preferably by filtration. Optionally, the isolated crystals may be washed with a solvent. Preferably, the solvent comprises acetone and most preferably, the solvent is acetone.

Finally, the valbenazine dihydrochloride crystals may optionally be dried at a temperature in the range of from 20 to 60° C., more preferably of from 20 to 40° C. and most preferably the crystals are dried at RT. Drying may be performed for a period of time in the range of from about 1 to 72 hours, preferably from about 2 to 48 hours, more preferably from about 4 to 24 hours and most preferably from about 6 to 18 hours. Drying may be performed at ambient pressure and/or under vacuum preferably at about 100 mbar or less, more preferably at about 50 mbar or less and most preferably at about 30 mbar or less.

The Third Crystalline Form of Valbenazine Dihydrochloride of the Present Invention The present invention relates to a crystalline form of valbenazine dihydrochloride of Formula (VIII), (IX) or (X), characterized by having a powder X-ray diffractogram comprising reflections at 2-Theta angles of:

(4.2±0.2)°, (4.7±0.2)° and (13.3±0.2)°; or
(4.2±0.2)°, (4.7±0.2)°, (8.6±0.2)° and (13.3±0.2)°; or
(4.2±0.2)°, (4.7±0.2)°, (8.6±0.2)°, (9.5±0.2)° and (13.3±0.2)°; or
(4.2±0.2)°, (4.7±0.2)°, (8.6±0.2)°, (9.5±0.2)°, (13.3±0.2)° and (14.1±0.2)°; or
(4.2±0.2)°, (4.7±0.2)°, (7.6±0.2)°, (8.6±0.2)°, (9.5±0.2)°, (13.3±0.2)° and (14.1±0.2)°; or
(4.2±0.2)°, (4.7±0.2)°, (7.6±0.2)°, (8.4±0.2)°, (8.6±0.2)°, (9.5±0.2)°, (13.3±0.2)° and (14.1±0.2)°; or
(4.2±0.2)°, (4.7±0.2)°, (7.6±0.2)°, (8.4±0.2)°, (8.6±0.2)°, (9.5±0.2)°, (13.3±0.2)°, (14.1±0.2)° and (14.6±0.2)°; or
(4.2±0.2)°, (4.7±0.2)°, (7.6±0.2)°, (8.4±0.2)°, (8.6±0.2)°, (9.5±0.2)°, (13.3±0.2)°, (14.1±0.2)°, (14.6±0.2)° and (18.3±0.2)°;

when measured at a temperature in the range of from 20 to 30° C. with Cu-Kalpha1,2 radiation having a wavelength of 0.15419 nm.

In another embodiment, the present invention relates to a crystalline form of valbenazine dihydrochloride of Formula (VIII), (IX) or (X), characterized by having a powder X-ray diffractogram comprising reflections at 2-Theta angles of:

(4.2±0.1)°, (4.7±0.1)° and (13.3±0.1)°; or
(4.2±0.1)°, (4.7±0.1)°, (8.6±0.1)° and (13.3±0.1)°; or
(4.2±0.1)°, (4.7±0.1)°, (8.6±0.1)°, (9.5±0.1)° and (13.3±0.1)°; or
(4.2±0.1)°, (4.7±0.1)°, (8.6±0.1)°, (9.5±0.1)°, (13.3±0.1)° and (14.1±0.1)°; or
(4.2±0.1)°, (4.7±0.1)°, (7.6±0.1)°, (8.6±0.1)°, (9.5±0.1)°, (13.3±0.1)° and (14.1±0.1)°; or (4.2±0.1)°, (4.7±0.1)°, (7.6±0.1)°, (8.4±0.1)°, (8.6±0.1)°, (9.5±0.1)°, (13.3±0.1)° and (14.1±0.1)°; or (4.2±0.1)°, (4.7±0.1)°, (7.6±0.1)°, (8.4±0.1)°, (8.6±0.1)°, (9.5±0.1)°, (13.3±0.1)°, (14.1±0.1)° and (14.6±0.1)°; or (4.2±0.1)°, (4.7±0.1)°, (7.6±0.1)°, (8.4±0.1)°, (8.6±0.1)°, (9.5±0.1)°, (13.3±0.1)°, (14.1±0.1)°, (14.6±0.1)° and (18.3±0.1)°;

when measured at a temperature in the range of from 20 to 30° C. with Cu-Kalpha1,2 radiation having a wavelength of 0.15419 nm.

Figure 9:
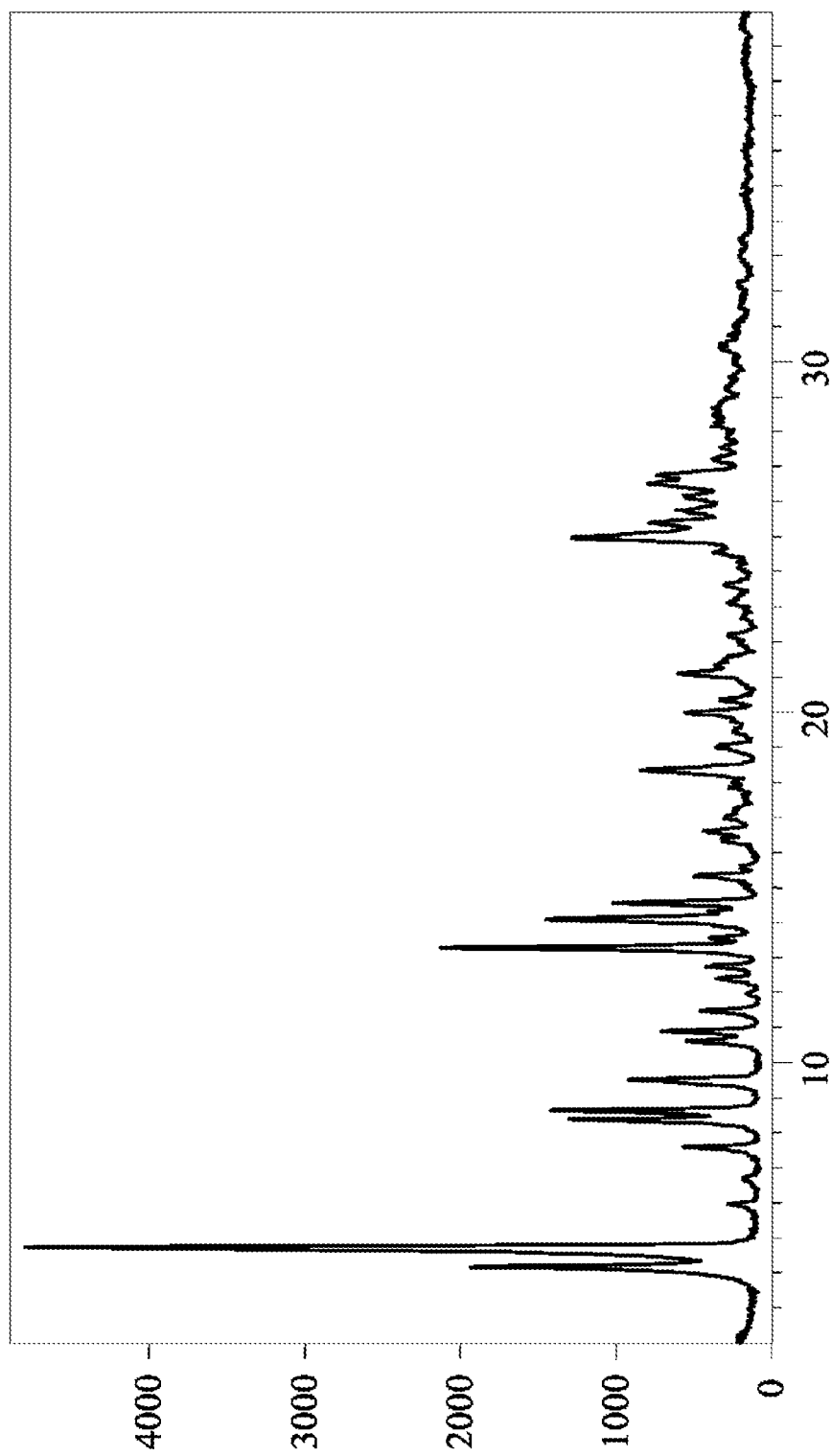
FIG. 9: illustrates a representative powder X-ray diffractogram of the third crystalline form of valbenazine dihydrochloride according to the present invention. The x-axis shows the scattering angle in ° 2-Theta, the y-axis shows the intensity of the scattered X-ray beam in counts of detected photons.

In another embodiment, the present invention relates to a crystalline form of valbenazine dihydrochloride of Formula (VIII), (IX) or (X), characterized by having a powder X-ray diffractogram essentially the same as shown in FIG. 9 of the present invention, when measured at a temperature in the range of from 20 to 30° C. with Cu-Kalpha1,2 radiation having a wavelength of 0.15419 nm.

In a further aspect, the invention relates to a process for the preparation of the third crystalline form of valbenazine dihydrochloride of Formula (VIII), (IX) or (X) as defined above comprising:

(a) providing a solution comprising valbenazine dihydrochloride and water; and (b) crystallizing valbenazine dihydrochloride from the solution provided in step (a); and (c) separating at least a part of the crystals obtained in step (b) from the mother liquor; and (d) optionally, drying the crystals obtained in step (c).

Valbenazine may be prepared according to the process described in Example 2 of WO 2008/058261 A1 (compound 2-1) and hydrochloric acid is commercially available. Alternatively, deuterated valbenazine is used. This compound is e.g. disclosed in WO 2014/120654 and can be prepared according to the methods disclosed therein. In general, deuterated valbenazine can be produced by providing tetrabenazine or deutetrabenazine (WO 2010/044981, WO 2011/153157, WO 2015/084622) followed by reduction of the ketone to the corresponding alcohol, conjugation with N-protected L-valine and final removal of the N-protecting group. Alternatively, deuterated valbenazine can be accessed starting from (+)-tetrabenazine via selective removal of the methoxy group under acidic conditions (see Brossi et al. Helvetica Chimica Acta (1958), 16, p. 119f) followed by alkylation with a deuterated methylating agent such as D3Cl or (D3CO)2SO2, followed by the final assembly.

Valbenazine dihydrochloride, which is used as starting material in step (a) of the above described process may be prepared by reacting valbenazine or deuterated valbenazine with hydrochloric acid in a suitable solvent. The valbenazine dihydrochloride starting material may be prepared according to the procedure provided in Example 16 herein, leading to amorphous material.

In step (a) a solution of valbenazine dihydrochloride in a solvent comprising water is prepared. The solvent may additionally comprise one or more C1-C3 alcohols such as methanol, ethanol, n-propanol and/or isopropanol. Preferably, water is the only solvent present. The solution is preferably prepared by heating valbenazine dihydrochloride in water e.g. to a temperature in the range of from 30 to 60° C., preferably of from 40 to 50° C. Once, a solution is obtained, it may optionally be filtrated in order to remove any undissolved particles. The final valbenazine dihydrochloride concentration of the solution obtained in step (a) is preferably in the range of from 100 to 700 g/L, more preferably of from 400 to 600 g/L, for example the final concentration is 500 g/L.

In step (b) of the above described process the valbenazine dihydrochloride is crystallized from the solution obtained in step (a). Thereby, crystallization may occur spontaneously by leaving the solution with or without slurrying, wherein slurrying in the context of the present invention relates to any motion of the mixture comprising valbenazine dihydrochloride, which is caused by stirring, shaking and/or ultrasonic irradiation. In order to accelerate the crystallization, the solution may be naturally or actively cooled to room temperature or a temperature in the range of from −10 to +20° C., for example of from 0 to 10° C. Crystallization may also be initiated by adding seed crystals to the solution. Seed crystals can be prepared according to Example 3 herein. The amount of seed crystals applied may range from 1 to 20 weight %, preferably from 2 to 5 weight %, based on the weight of the valbenazine dihydrochloride present in the solution.

Once crystallization occurred the obtained suspension is optionally further kept at a temperature in the range of from −10 to +20° C., for example of from 0 to 10° C. to increase the yield before the valbenazine dihydrochloride crystals are separated from the mother liquor by any conventional method such as filtration or centrifugation, most preferably by filtration. Optionally, the isolated crystals may be washed with a solvent. Preferably, the solvent comprises acetone and most preferably, the solvent is acetone.

Finally, the valbenazine dihydrochloride crystals may optionally be dried at room temperature. Drying may be performed for a period of time in the range of from about 1 to 72 hours, preferably from about 2 to 48 hours, more preferably from about 4 to 24 hours and most preferably from about 6 to 18 hours. Drying is preferably performed at ambient pressure.

Composition Comprising Crystalline Valbenazine Dihydrochloride

In another aspect, the invention relates to a composition comprising the crystalline valbenazine dihydrochloride as defined above, in particular one of the crystalline forms of valbenazine dihydrochloride as defined above, which composition is essentially free of any other physical form of valbenazine dihydrochloride.

In a preferred embodiment, the invention relates to a composition comprising the crystalline valbenazine dihydrochloride as defined above, in particular one of the crystalline forms of valbenazine dihydrochloride as defined above, characterized by comprising at most 20 weight %, preferably at most 10 weight %, more preferably at most 5 weight %, even more preferably at most 2 weight % and most preferably at most 1 weight % of any other physical form of valbenazine dihydrochloride, based on the total weight of the composition. In a particular preferred embodiment, the any other physical form is amorphous valbenazine dihydrochloride.

In another embodiment, the invention relates to a composition comprising at least 90 weight % of the crystalline valbenazine dihydrochloride as defined above, in particular one of the crystalline forms of valbenazine dihydrochloride as defined above, based on the total weight of the composition. Preferably, the composition comprises less than 5 weight % amorphous valbenazine dihydrochloride, such as less than 2 weight % amorphous valbenazine dihydrochloride. For example, the composition comprises 2 to 4 weight %, preferably 0.5 to 1.5 weight % amorphous valbenazine dihydrochloride.

In a further embodiment, the invention relates to a composition comprising at least 95 weight % of the crystalline valbenazine dihydrochloride as defined above, in particular one of the crystalline forms of valbenazine dihydrochloride as defined above, based on the total weight of the composition. Preferably, the composition comprises less than 4 weight % amorphous valbenazine dihydrochloride, such as less than 2 weight % amorphous valbenazine dihydrochloride. For example, the composition comprises 2 to 3 weight %, preferably 0.5 to 1.5 weight % amorphous valbenazine dihydrochloride.

In a preferred embodiment, the invention relates to a composition consisting essentially of the crystalline valbenazine dihydrochloride as defined above. In another preferred embodiment, the invention relates to a composition consisting essentially of one of the crystalline forms of valbenazine dihydrochloride as defined above.

Pharmaceutical Composition Comprising Crystalline Valbenazine Dihydrochloride

In another aspect, the invention relates to the use of the crystalline valbenazine dihydrochloride, in particular one of the crystalline forms of valbenazine dihydrochloride as defined above for the preparation of a pharmaceutical composition. Furthermore, the invention relates to the use of the crystalline valbenazine dihydrochloride, in particular one of the crystalline forms of valbenazine dihydrochloride as obtained by the above described processes for the preparation of a pharmaceutical composition. Moreover, the invention relates to the use of the composition comprising the crystalline valbenazine dihydrochloride, in particular one of the crystalline forms of valbenazine dihydrochloride as defined above for the preparation of a pharmaceutical composition. A more detailed description of pharmaceutical compositions is described for crystalline valbenazine ditosylate below. The invention also relates to pharmaceutical compositions as described below for the ditosylate, wherein the crystalline valbenazine ditosylate is to be replaced by valbenazine dihydrochloride of the present invention, and in particular by the second crystalline form of valbenazine dihydrochloride of the present invention.

Pharmaceutical Composition Comprising Crystalline Valbenazine Ditosylate

In another aspect, the invention relates to the use of the crystalline valbenazine ditosylate, in particular of the crystalline hydrate or the crystalline anhydrate of valbenazine ditosylate of the present invention as defined above for the preparation of a pharmaceutical composition. Furthermore, the invention relates to the use of the crystalline valbenazine ditosylate, in particular of the crystalline hydrate or the crystalline anhydrate of valbenazine ditosylate of the present invention as obtained by the above described processes for the preparation of a pharmaceutical composition. Moreover, the invention relates to the use of the composition comprising the crystalline valbenazine ditosylate, in particular the crystalline hydrate or the crystalline anhydrate of valbenazine ditosylate of the present invention as defined above for the preparation of a pharmaceutical composition.

The pharmaceutical composition may be prepared by pharmaceutical standard procedures e.g. by wet or dry processing methods. In certain embodiments the pharmaceutical composition is prepared by wet processing methods, such as, but not limited to, wet granulation methods. Suitable wet granulation methods comprise high-shear granulation or fluid bed granulation. In another embodiment the pharmaceutical composition is prepared by dry processing methods, such as, but not limited to, direct compression or dry granulation methods. An example of dry granulation is roller compaction. The pharmaceutical composition obtained by dry or wet processing methods are preferably compressed into tablets or encapsulated.

In a further aspect the invention relates to a pharmaceutical composition comprising crystalline valbenazine ditosylate, in particular the crystalline hydrate or the crystalline anhydrate of valbenazine ditosylate as defined above or the composition comprising the same as defined above and at least one pharmaceutically acceptable excipient. Preferably, the at least one pharmaceutically acceptable excipient is selected from the group consisting of binders, fillers, diluents, disintegrants, lubricants, glidants, coloring agents, flavouring agents, sweetening agents, emulsifying agents, dispersing agents, wetting agents and film coatings.

In one embodiment, suitable binders which may be used for the pharmaceutical composition of the present invention include, but are not limited to starches such as corn starch, potato starch and pre-gelatinized starch (e.g. STARCH 1500); gelatin, sugars such as sucrose, glucose, dextrose, molasses and lactose; natural and synthetic gums such as acacia, alginic acid, alginates, extract of irish moss, panwar gum, ghatti gum, mucilage of isabgol husks, carboxymethylcellulose, methylcellulose; polyinylpyrrolidone (PVP), veegum, larch arabogalactan, powdered tragacanth and guar gum; celluloses such as ethyl cellulose, cellulose acetate, carboxymethyl cellulose calcium, sodium carboxymethyl cellulose, methyl cellulose, hydroxyethyl cellulose (HEC), hydroxypropylcellulose (HPC), hydroxypropyl methyl cellulose (HPMC); microcrystalline celluloses such as AVICEL-PH-101, AVICEL-PH-103, AVICEL RC-581, AVICEL-PH-105 (FMC Corp., Marcus Hook, Pa.); and mixtures thereof.

In another embodiment, suitable fillers which may be used for the pharmaceutical composition of the present invention include, but are not limited to talc, calcium carbonate, microcrystalline cellulose, powdered cellulose, dextrates, kaolin, mannitol, silicic acid, sorbitol, starch, pregelatinized starch, and mixtures thereof.

In another embodiment, suitable diluents which may be used for the pharmaceutical composition of the present invention include, but are not limited to dicalcium phosphate, calcium sulfate, lactose, sucrose, inositol, cellulose, kaolin, mannitol, sodium chloride, dry starch and powdered sugar.

In a further embodiment, suitable disintegrants which may be used for the pharmaceutical composition of the present invention include, but are not limited to agar, bentonite, celluloses such as methylcellulose and carboxymethylcellulose; wood products; natural sponge; cation-exchange resins; alginic acid; gums such as guar gum and Vee gum HV; citrus pulp; cross-linked celluloses such as crosscarmellose; cross-linked polymers such as crospovidone; cross-linked starches; calcium carbonate; microcrystalline cellulose; sodium starch glycolate; polacrilin potassium; starches such as corn starch, potato starch, tapioca starch and pregelatinized starch; clays; aligns; and mixtures thereof;

In still a further embodiment, suitable lubricants which may be used for the pharmaceutical composition of the present invention include, but are not limited to calcium stearate, magnesium stearate, mineral oil, light mineral oil, glycerin, sorbitol, mannitol, glycols such as glycerol behenate and polyethylene glycol (PEG); stearic acid, sodium laryl sulfate, talc, hygrogenated vegetable oil including, peanut oil, cottonseed oil, sunflower oil, sesame oil, olive oil, corn oil and soybean oil; zinc stearate, ethyl oleate, ethyl laureate, agar, starch, lycopodium, silica or silica gels such as AEOROSIL® 200 (W.R. Grace Co., Baltimore, Md.) and CAB-0-SIL® (Cabot Co. of Boston, Mass.); and mixtures thereof In even a further embodiment, suitable glidants which may be used for the pharmaceutical composition of the present invention include, but are not limited to colloidal silicon dioxide, CAB-0-SIL® (Cabot Co. of Boston, Mass.) and asbestos-free talc.

It should be understood that many excipients may serve several functions, event within the same formulation.

In one embodiment, the present invention relates to a pharmaceutical composition as defined above, wherein the predetermined and/or pharmaceutically effective amount of crystalline valbenazine ditosylate of the present invention is in the range of from about 5 to 150 mg, calculated as water free valbenazine. Preferably, the predetermined and/or pharmaceutically effective amount of the crystalline valbenazine ditosylate of the present invention is selected from the group consisting of 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg and 150 mg, calculated as water free valbenazine. More preferably, the predetermined and/or pharmaceutically effective amount of the crystalline valbenazine ditosylate of the present invention is selected from the group consisting of 25 mg, 40 mg, 50 mg, 75 mg, 80 mg and 100 mg, calculated as water free valbenazine. Even more preferably, the predetermined and/or pharmaceutically effective amount of the crystalline valbenazine ditosylate of the present invention is 40 or 80 mg, most preferably 40 mg, calculated as water free valbenazine.

In one embodiment, the invention relates to a pharmaceutical composition as defined above, which is an oral solid dosage form. Preferably, the oral solid dosage form is a capsule or a tablet, more preferably a tablet and most preferably a film-coated tablet.

Preferably, the present invention relates to a pharmaceutical composition as defined above, wherein the pharmaceutical composition is to be administered once-daily.

In still another aspect the invention relates to the pharmaceutical composition as defined above for use as a medicament.

In a further aspect the invention relates to the pharmaceutical composition as defined above for use in the treatment of hyperkinetic disorders. In a preferred embodiment, the hyperkinetic disorder is tardive dyskinesia.

In a preferred embodiment of the present invention the dosage form of the present invention is packed by a suitable packaging material. The packaging material preferably reduces or prevents water exchange between the pharmaceutical composition of the present invention and the environment. For example, if the dosage forms are tablets or capsules, suitable blister pack materials can be used. The blister pack may comprise a cavity or pocket, preferably containing a thermoformed plastic. This usually has as a backing a lidding seal containing an aluminum and/or plastic foil. Further, if the composition is in form of a granulate, suitable sachets can be used.

In a particularly preferred embodiment the pharmaceutical composition or the dosage form of the present invention is packed by a material having a water vapor permeability of 0.001 to 0.15 g/m$^2$/day at 38° C./5%/90% RH, preferably of 0.01 to 0.12 g/m$^2$/day at 38° C./5%/90% RH, in particular 0.05 to 0.10 g/m$^2$/day at 38° C./5%/90% RH, wherein said water vapor permeability is determined according to ASTM F1249-13. Preferably, a Permatran-W Model 3/33 device is used. The measurement is preferably carried out at 38° C.

Further, preferably the humidity in the dry chamber is 5% relative humidity (=RH), whereas the humidity in the wet chamber is 90% RH.

In a preferred embodiment the packaging material can preferably be selected from polyvinylchloride (PVC), polyvinylidene chloride (PVDC), polyethylene (PE), polypropylene (PP), polyethylene terephthalate (PET) polystyrol (PS), polyamide and alumina or combinations thereof.

In a preferred embodiment the packing material comprises layered sheets, which can be thermoformed, containing one or more layers. In a preferred embodiment the packing material can be a composite material, e.g. coextruded composite material, e.g. a polyamide-alumina-polyvinyl chloride composite material, which is also referred to as Nylon®-Alu-PVC.

In a preferred embodiment the packaging material has a thickness of 1 μm to 1 mm. In case of a blister pack the thermoformed plastic pocket preferably has a thickness of 100 to 1000 μm, more preferably of 150 to 800 μm. Further, the backing foil usually has a thickness of 10 to 150 μm, more preferably of 15 to 100 μm.

EXAMPLES

The following examples are illustrative for the disclosure and shall not limit the scope of the invention.

Example 1: Preparation of Crystalline Valbenazine Ditosylate Hydrate

A solution of valbenazine (200 mg, 0.48 mmol, e.g. prepared according to Example 2 of WO 2008/058261 A1) in toluene (5 mL) was added to a suspension of p-toluenesulfonic acid monohydrate (200 mg, 1.05 mmol) in toluene (5 mL) in a dropwise fashion. The reaction mixture was stirred for 24 hours at room temperature yielding valbenazine ditosylate as white mass with a jelly-like consistency. After evaporating the toluene (rotary evaporator, 40° C./50 mbar) valbenazine ditosylate hydrate was obtained as white crystalline powder. The thus obtained material was characterized by PXRD, DSC and GMS (see Examples 2 to 4).

Example 2: Powder X-Ray Diffraction

The powder X-ray diffractogram was obtained with an X'Pert PRO diffractometer (PANalytical, Almelo, The Netherlands) equipped with a theta/theta coupled goniometer in transmission geometry, programmable XYZ stage with well plate holder, Cu-Kalpha1,2 radiation source (wavelength 0.15419 nm) with a focussing mirror, a 0.5° divergence slit, a 0.02° soller slit collimator and a 0.5° anti-scattering slit on the incident beam side, a 2 mm anti-scattering slit, a 0.02° soller slit collimator, a Ni-filter and a solid state PIXcel detector on the diffracted beam side. The diffractogram was recorded at a tube voltage of 40 kV, tube current of 40 mA, applying a step size of 0.013° 2-Theta with 80 s per step in the angular range of 2° to 40° 2-Theta.

A typical precision of the 2-Theta values is in the range of ±0.2° 2-Theta, preferably in the range of ±0.1° 2-Theta. Thus, the reflection of the crystalline hydrate of valbenazine ditosylate of the present invention that appears for example at 5.7° 2-Theta can appear between 5.5° and 5.9° 2-Theta, preferably between 5.6° and 5.8° 2-Theta on most X-ray diffractometers under standard conditions.

A representative powder X-ray diffractogram of the crystalline hydrate of valbenazine ditosylate of the present invention is displayed in FIG. 1 herein and the corresponding reflection list is provided in Table 1 below.

TABLE 1

PXRD reflections and corresponding relative intensities of the valbenazine ditosylate hydrate prepared according to Example 1 in the range of from 2 to 30° 2-Theta; A typical precision of the 2-Theta values is in the range of ±0.2° 2-Theta, preferably of ±0.1° 2-Theta.

| Angle [°2-Theta] | Relative Intensity [%] |
|---|---|
| 5.7 | 100 |
| 7.1 | 9 |
| 7.6 | 4 |
| 10.2 | 12 |
| 10.4 | 5 |
| 11.0 | 2 |
| 11.4 | 5 |
| 14.3 | 18 |
| 15.3 | 18 |
| 16.0 | 23 |
| 16.9 | 17 |
| 17.5 | 6 |
| 17.9 | 12 |
| 18.4 | 9 |
| 18.6 | 31 |
| 19.3 | 2 |
| 19.9 | 6 |
| 20.3 | 5 |
| 20.6 | 8 |
| 20.9 | 6 |
| 21.8 | 5 |
| 22.6 | 16 |
| 22.9 | 10 |
| 23.7 | 2 |
| 24.0 | 2 |
| 24.7 | 2 |
| 25.3 | 1 |
| 26.5 | 8 |
| 26.7 | 9 |
| 27.6 | 5 |
| 28.7 | 3 |
| 29.9 | 3 |

Example 3: Differential Scanning Calorimetry

Differential scanning calorimetry (DSC) was performed with a DSC 7 (Perkin-Elmer, Norwalk, Conn., USA) using a Pyris 2.0 software. 4.7307±0.0005 mg sample (using a UM3 ultramicrobalance, Mettler, Greifensee, CH) were weighed into Al-Pans (25 microliter) and sealed with a cover, which was perforated by a needle. The sample was heated at a rate of 10 K/min. Dry nitrogen was used as the purge gas (purge rate: 20 mL/min).

Figure 2:
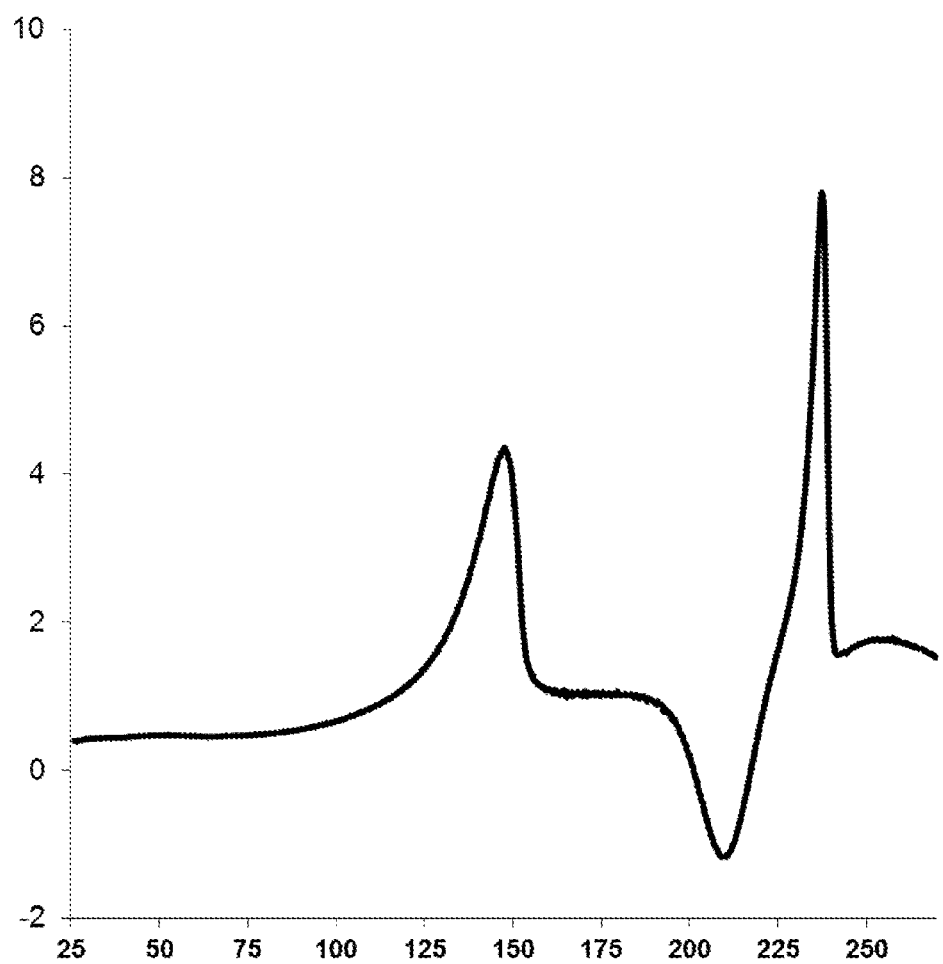
FIG. 2: illustrates a representative DSC curve of the crystalline hydrate of valbenazine ditosylate according to the present invention. The x-axis shows the temperature in degree Celsius (° C.), the y-axis shows the heat flow in Watt per gram (W/g) with endothermic peaks going up.

The corresponding DSC curve is displayed in FIG. 2 of the present invention and displays a first endothermic peak having an onset temperature of about 131° C. and a peak temperature of about 148° C. Thereafter an exothermic peak having an onset temperature of about 196° C. and a peak temperature of about 211° C. appears immediately followed by a second endothermic peak having an onset temperature of about 231° C. and a peak temperature of about 238° C. The DSC curve may be interpreted in that the first endothermic peak corresponds to a dehydration/melting event, the exothermic peak is a crystallization peak and the second endothermic peak corresponds to a melting event.

Example 4: Gravimetric Moisture Sorption Experiment

The moisture sorption curve was recorded with a SPS-11 moisture sorption analyzer (MD Messtechnik, Ulm, D). The measurement was started at 0% RH and increased up to 90% RH in 5% steps. The equilibrium condition for each step was set to a mass constancy of ±0.001% over 50 min. The temperature was 25±0.1° C.

TABLE 2

Mass change (dm) determined at different relative humidities (RHs) and corresponding amount of water in moles

| RH [%] | dm [%] | mol $H_2O$ |
|---|---|---|
| 0 | 0.00 | 0.00 |
| 5 | 0.36 | 0.15 |
| 10 | 0.62 | 0.26 |
| 15 | 0.84 | 0.36 |
| 20 | 1.06 | 0.45 |
| 25 | 1.27 | 0.54 |
| 30 | 1.45 | 0.62 |
| 35 | 1.64 | 0.70 |
| 40 | 1.85 | 0.78 |
| 45 | 2.08 | 0.88 |
| 50 | 2.32 | 0.98 |
| 55 | 2.61 | 1.11 |
| 60 | 2.95 | 1.25 |
| 65 | 3.34 | 1.42 |
| 70 | 3.81 | 1.61 |
| 75 | 4.46 | 1.89 |
| 80 | 5.27 | 2.23 |

Example 5: Preparation of Crystalline Valbenazine Ditosylate Anhydrate

A solution of valbenazine (200 mg, 0.48 mmol, e.g. prepared according to Example 2 of WO 2008/058261 A1) in butyl acetate (10 mL) was added to a suspension of p-toluenesulfonic acid monohydrate (200 mg, 1.05 mmol) in butyl acetate (10 mL) in a dropwise fashion. The reaction mixture was stirred for 12 hours at room temperature before the obtained crystals were collected by filtration, washed with butyl acetate (5 mL) and dried at 40° C. for 2 hours to obtain crystalline anhydrous valbenazine ditosylate (289 mg). The thus obtained material was characterized by PXRD, DSC and GMS (see Examples 6 to 8).

Example 6: Powder X-Ray Diffraction

The powder X-ray diffractogram was obtained with an X'Pert PRO diffractometer (PANalytical, Almelo, The Netherlands) equipped with a theta/theta coupled goniometer in transmission geometry, programmable XYZ stage with well plate holder, Cu-Kalpha1,2 radiation source (wavelength 0.15419 nm) with a focussing mirror, a 0.5° divergence slit, a 0.02° soller slit collimator and a 0.5° anti-scattering slit on the incident beam side, a 2 mm anti-scattering slit, a 0.02° soller slit collimator, a Ni-filter and a solid state PIXcel detector on the diffracted beam side. The diffractogram was recorded at a tube voltage of 40 kV, tube current of 40 mA, applying a step size of 0.013° 2-Theta with 80 s per step in the angular range of 2° to 40° 2-Theta. A typical precision of the 2-Theta values is in the range of ±0.2° 2-Theta, preferably in the range of ±0.1° 2-Theta. Thus, the reflection of the crystalline anhydrate of valbenazine ditosylate of the present invention that appears for example at 6.3° 2-Theta can appear between 6.1° and 6.5° 2-Theta, preferably between 6.2° and 6.4° 2-Theta on most X-ray diffractometers under standard conditions.

A representative powder X-ray diffractogram of the crystalline anhydrate of valbenazine ditosylate of the present invention is displayed in FIG. 4 herein and the corresponding reflection list is provided in Table 3 below.

TABLE 3

PXRD reflections and corresponding relative intensities of the valbenazine ditosylate anhydrate prepared according to Example 5 in the range of from 2 to 30° 2-Theta; A typical precision of the 2-Theta values is in the range of ±0.2° 2-Theta, preferably of ±0.1° 2-Theta.

| Angle [°2-Theta] | Relative Intensity [%] |
|---|---|
| 5.3 | 3 |
| 6.3 | 100 |
| 8.5 | 2 |
| 11.3 | 3 |
| 11.5 | 3 |
| 12.6 | 4 |
| 12.8 | 4 |
| 13.8 | 3 |
| 15.6 | 15 |
| 16.2 | 3 |
| 16.6 | 7 |
| 16.9 | 4 |
| 17.1 | 7 |
| 17.9 | 25 |
| 18.2 | 9 |
| 18.4 | 6 |
| 19.8 | 27 |
| 20.0 | 6 |
| 20.2 | 3 |
| 20.6 | 5 |
| 20.9 | 3 |
| 21.4 | 3 |
| 22.1 | 4 |
| 22.6 | 8 |
| 22.7 | 8 |
| 23.1 | 7 |
| 23.4 | 4 |
| 24.4 | 4 |
| 24.6 | 4 |
| 24.9 | 3 |
| 25.3 | 3 |
| 25.7 | 2 |
| 26.3 | 3 |
| 27.8 | 2 |
| 28.1 | 2 |

Example 7: Differential Scanning Calorimetry

Differential scanning calorimetry (DSC) was performed with a DSC 7 (Perkin-Elmer, Norwalk, Conn., USA) using a Pyris 2.0 software. 7.115±0.0005 mg sample (using a UM3 ultramicrobalance, Mettler, Greifensee, CH) were weighed into Al-Pans (25 microliter) and sealed with a cover, which was perforated by a needle. The sample was heated at a rate of 10 K/min. Dry nitrogen was used as the purge gas (purge rate: 20 mL/min).

Figure 5:
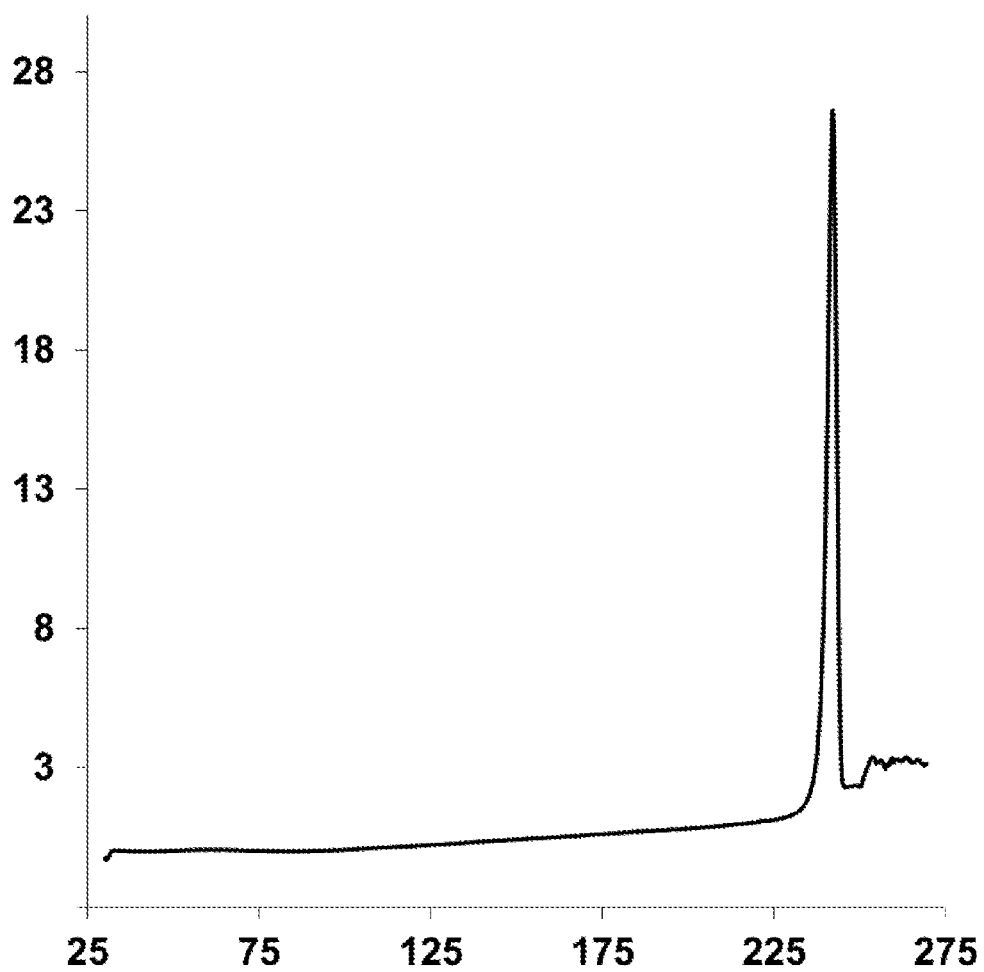
FIG. 5: illustrates a representative DSC curve of the crystalline anhydrate of valbenazine ditosylate according to the present invention. The x-axis shows the temperature in degree Celsius (° C.), the y-axis shows the heat flow in Watt per gram (W/g) with endothermic peaks going up.

The corresponding DSC curve of the crystalline anhydrous form of valbenazine ditosylate of the present invention is shown in FIG. 5 and displays a single endothermic peak having an onset temperature of 239.4° C., a peak temperature of 242.4° C. and a heat of fusion of 54.1 kJ/mol. The DSC curve may be interpreted in that the endothermic peak corresponds to a melting event.

Example 8: Thermogravimetric Analysis

TGA was performed with thermogravimetric-system TGA-7 using Pyris-Software for Windows NT, (Perkin-Elmer, Norwalk, Conn., USA). The sample (10.28 mg) was weighed in a platinum-sample holder (50 μL) and heated from room temperature to 200° C. at a heating rate of 10 K/min. Nitrogen was used as the purge gas (sample purge: 20 mL/min, balance purge: 40 mL/min).

Crystalline valbenazine ditosylate obtained from Example 5 herein showed only a slight mass loss (0.3 w-% up to a temperature of 140° C.) indicating the presence of an anhydrous and solvent free form. The corresponding TGA curve is displayed in FIG. 6 herein.

Example 9: Preparation of Crystalline Valbenazine Ditosylate Anhydrate

A solution of valbenazine (200 mg, 0.48 mmol, e.g. prepared according to Example 2 of WO 2008/058261 A1) in diethyl ether (10 mL) was added to a suspension of p-toluenesulfonic acid monohydrate (200 mg, 1.05 mmol) in diethyl ether (10 mL) in a dropwise fashion. The reaction mixture was stirred for 12 hours at room temperature before the obtained crystals were collected by filtration and dried at 40° C. for 2 hours to obtain crystalline anhydrous valbenazine ditosylate (278 mg).

Example 10: Preparation of Crystalline Valbenazine Ditosylate Anhydrate

A solution of valbenazine (3000 mg, 7.20 mmol, e.g. prepared according to Example 2 of WO 2008/058261 A1) in diethyl ether (200 mL) was added to a suspension of p-toluenesulfonic acid monohydrate (3000 mg, 15.75 mmol) in diethyl ether (200 mL) in a dropwise fashion. The reaction mixture was stirred for 12 hours at room temperature before the obtained crystals were collected by filtration, washed with diethyl ether (10 mL) and dried at 40° C. for 2 hours to obtain crystalline anhydrous valbenazine ditosylate (5020 mg).

Example 11: Preparation of Crystalline Valbenazine Ditosylate Anhydrate

A solution of valbenazine (200 mg, 0.48 mmol, e.g. prepared according to Example 2 of WO 2008/058261 A1) in diisopropyl ether (10 mL) was added to a suspension of p-toluenesulfonic acid monohydrate (200 mg, 1.05 mmol) in diisopropyl ether (10 mL) in a dropwise fashion. The reaction mixture was stirred for 12 hours at room temperature before the obtained crystals were collected by filtration and dried at 40° C. for 2 hours to obtain crystalline anhydrous valbenazine ditosylate (220 mg).

Example 12: Preparation of Crystalline Valbenazine Ditosylate Anhydrate

A solution of valbenazine (200 mg, 0.48 mmol, e.g. prepared according to Example 2 of WO 2008/058261 A1) in acetonitrile (10 mL) was added to a suspension of p-toluenesulfonic acid monohydrate (200 mg, 1.05 mmol) in acetonitrile (10 mL) in a dropwise fashion. The reaction mixture was stirred for 12 hours at room temperature before the obtained crystals were collected by filtration and dried at 40° C. for 2 hours to obtain crystalline anhydrous valbenazine ditosylate (287 mg).

Example 13: Preparation of the First Crystalline Form of Valbenazine Dihydrochloride A mixture of amorphous valbenazine dihydrochloride (2000 mg, e.g. prepared according to Example 16 herein) and acetone (200 mL) was heated to reflux temperature thereby obtaining a clear solution. After a few minutes at reflux temperature, valbenazine dihydrochloride crystals were obtained. The suspension was allowed to cool to room temperature and further stirred for 24 hours, before the crystals were collected by filtration and finally dried at 40° C. under vacuum (30 mbar) for 18 hours. The thus obtained material was characterized by powder X-ray diffraction and a representative powder X-ray diffractogram of said material is displayed in FIG. 7 herein. The corresponding reflection list is provided in Table 4 below.

TABLE 4 powder X-ray reflections and corresponding relative intensities of valbenazine dihydrochloride prepared according to Example 13 in the range of from 2 to 30° 2-Theta; A typical precision of the 2-Theta values is in the range of ±0.2° 2-Theta, preferably of ±0.1° 2-Theta.

| Angle [°2-Theta] | Relative Intensity [%] |
| --- | --- |
| 6.9 | 18 |
| 7.2 | 100 |
| 8.2 | 2 |
| 9.2 | 34 |
| 10.7 | 11 |
| 12.7 | 24 |
| 14.1 | 10 |
| 15.1 | 10 |
| 17.5 | 12 |
| 18.1 | 46 |
| 18.4 | 10 |
| 19.7 | 4 |
| 20.1 | 10 |
| 20.9 | 13 |
| 21.5 | 4 |
| 22.5 | 21 |
| 22.6 | 28 |
| 23.4 | 14 |
| 24.0 | 10 |
| 24.3 | 5 |
| 25.4 | 4 |
| 26.0 | 23 |
| 27.2 | 2 |
| 27.7 | 2 |
| 29.2 | 2 |
| 29.7 | 4 |
| 30.0 | 4 |

Example 14: Preparation of the Second Crystalline Form of Valbenazine Dihydrochloride Amorphous valbenazine dihydrochloride (1000 mg, e.g. prepared according to Example 16 herein) was suspended in acetone (20 mL) and stirred at 40° C. for 10 hours. The obtained crystals were collected by filtration and dried at 40° C. under vacuum (30 mbar) for 18 hours. The thus obtained material was characterized by powder X-ray diffraction and a representative powder X-ray diffractogram of said material is displayed in FIG. 8 herein. The corresponding reflection list is provided in Table 5 below.

TABLE 5 powder X-ray reflections and corresponding relative intensities of valbenazine dihydrochloride prepared according to Example 14 in the range of from 2 to 30° 2-Theta; A typical precision of the 2-Theta values is in the range of ±0.2° 2-Theta, preferably of ±0.1° 2-Theta.

| Angle [°2-Theta] | Relative Intensity [%] |
| --- | --- |
| 12.0 | 100 |
| 14.3 | 5 |

TABLE 5-continued powder X-ray reflections and corresponding relative intensities of valbenazine dihydrochloride prepared according to Example 14 in the range of from 2 to 30° 2-Theta; A typical precision of the 2-Theta values is in the range of ±0.2° 2-Theta, preferably of ±0.1° 2-Theta.

| Angle [°2-Theta] | Relative Intensity [%] |
| --- | --- |
| 14.6 | 7 |
| 14.9 | 6 |
| 16.3 | 42 |
| 17.8 | 3 |
| 18.8 | 18 |
| 19.1 | 18 |
| 20.5 | 24 |
| 21.5 | 60 |
| 21.7 | 16 |
| 22.7 | 6 |
| 23.2 | 18 |
| 25.2 | 12 |
| 25.6 | 18 |
| 25.9 | 24 |
| 26.3 | 12 |
| 27.6 | 7 |
| 28.2 | 25 |
| 28.9 | 2 |

Example 15: Preparation of the Third Crystalline Form of Valbenazine Dihydrochloride Amorphous valbenazine dihydrochloride (490 mg, e.g. prepared according to Example 16 herein) was dissolved in water (1 mL) under slight heating. The obtained clear solution was allowed to stand at room temperature without stirring. After 24 hours, the obtained crystals were collected by filtration and air dried at room temperature. The thus obtained material was characterized by powder X-ray diffraction and a representative powder X-ray diffractogram of said material is displayed in FIG. 9 herein. The corresponding reflection list is provided in Table 6 below.

TABLE 6 powder X-ray reflections and corresponding relative intensities of valbenazine dihydrochloride prepared according to Example 15 in the range of from 2 to 30° 2-Theta; A typical precision of the 2-Theta values is in the range of ±0.2° 2-Theta, preferably of ±0.1° 2-Theta.

| Angle [°2-Theta] | Relative Intensity [%] |
| --- | --- |
| 4.2 | 39 |
| 4.7 | 100 |
| 6.0 | 4 |
| 6.7 | 2 |
| 7.6 | 10 |
| 8.4 | 25 |
| 8.7 | 28 |
| 9.5 | 18 |
| 10.6 | 10 |
| 10.9 | 13 |
| 11.5 | 8 |
| 12.4 | 5 |
| 12.8 | 6 |
| 13.3 | 43 |
| 13.6 | 6 |
| 14.1 | 28 |
| 14.6 | 19 |
| 15.3 | 8 |
| 16.4 | 5 |
| 16.6 | 7 |
| 18.3 | 15 |
| 19.0 | 5 |
| 20.0 | 9 |

TABLE 6-continued powder X-ray reflections and corresponding relative intensities of valbenazine dihydrochloride prepared according to Example 15 in the range of from 2 to 30° 2-Theta; A typical precision of the 2-Theta values is in the range of ±0.2° 2-Theta, preferably of ±0.1° 2-Theta.

| Angle [°2-Theta] | Relative Intensity [%] |
|---|---|
| 21.1 | 10 |
| 24.6 | 5 |
| 25.0 | 25 |
| 25.4 | 14 |
| 25.7 | 10 |
| 26.1 | 9 |
| 26.5 | 14 |
| 26.8 | 13 |
| 27.2 | 5 |
| 28.2 | 5 |
| 28.6 | 5 |

Example 16: Preparation of Amorphous Valbenazine Dihydrochloride

Valbenazine free base (5000 mg, e.g. prepared according to Example 2 of WO 2008/058261 A1) was dissolved in dry diethyl ether (150 mL). The slight turbid solution was filtrated through a syringe filter (pore size 0.44 microns) and added drop-wise to a solution of etheric hydrochloric acid (1M, 26 mL, 2.2 mol) and dry diethyl ether (20 mL) causing immediate precipitation of a white solid. The suspension was further stirred for 1 hour at room temperature, before the solid was collected by filtration, washed with diethyl ether (10 mL) and air dried to obtain amorphous valbenazine dihydrochloride.

The invention claimed is:

1. A crystalline valbenazine ditosylate characterized by the chemical structure according to Formula II

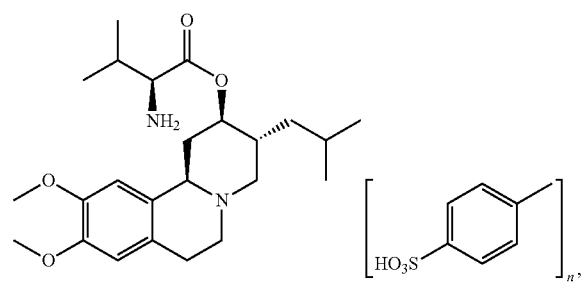

(II)

wherein n is in the range of from 1.7 to 2.3, which is an anhydrate characterized by having a powder X-ray diffractogram comprising reflections at 2-Theta angles of (6.3±0.2)°, (17.9±0.2)° and (19.8±0.2)°; or
(6.3±0.2)°, (15.6±0.2)°, (17.9±0.2)° and (19.8±0.2)°; or
(5.3±0.2)°, (6.3±0.2)°, (15.6±0.2)°, (17.9±0.2)° and (19.8±0.2)°;

when measured at a temperature in the range of from 20 to 30° C. with Cu-Kalpha$_{1,2}$ radiation having a wavelength of 0.15419 nm.

2. The crystalline valbenazine ditosylate anhydrate of claim 1 characterized by having a powder X-ray diffractogram essentially the same as shown in FIG. 4 of the present invention, when measured at a temperature in the range of from 20 to 30° C. with Cu-Kalpha$_{1,2}$ radiation having a wavelength of 0.15419 nm.

3. The crystalline valbenazine ditosylate anhydrate as defined in claim 1 characterized by having a differential scanning calorimetry curve comprising an endothermic peak having an onset temperature of (239±2) ° C. and a peak temperature of (242±2) ° C., when measured at a heating rate of 10 K/min.

4. A composition comprising at least 90 w-% of the crystalline valbenazine ditosylate anhydrate as defined in claim 1, based on the total weight of the composition.

5. The composition of claim 4 comprising less than 5 w-% amorphous valbenazine ditosylate.

6. Process for the preparation of the anhydrate as defined in claim 1 comprising:
(i) reacting valbenazine with p-toluenesulfonic acid monohydrate in toluene;
(ii) slurrying the reaction mixture of step (i);
(iii) removing toluene from the reaction mixture of step (i) or (ii).

7. The process of claim 6, optionally comprising:
step (iv) drying the crystals obtained in step (iii).

8. The process of claim 6, further comprising a step of mixing the crystalline valbenazine ditosylate anhydrate with one or more pharmaceutically acceptable excipient(s) to prepare a pharmaceutical composition.

9. The process of claim 8, wherein the pharmaceutical composition is prepared as an oral solid dosage form.

10. The process of claim 9, wherein the pharmaceutical composition has been packaged in packaging material having a thickness of 1 μm to 1 mm.

11. A method of therapeutic and/or prophylactic treatment, comprising a step of providing a crystalline valbenazine ditosylate as defined in claim 1, and a step of administering said crystalline form of valbenazine ditosylate to a person in need of such a treatment, wherein the treatment is hyperkinetic disorders.

12. The method according to claim 11, wherein the hyperkinetic disorder is tardive dyskinesia.

* * * * *